United States Patent
Chokai et al.

[11] Patent Number: 5,945,426
[45] Date of Patent: Aug. 31, 1999

[54] DERIVATIVES OF PYRIMIDINE FOR TREATING ACUTE CEREBROVASCULAR DISORDERS

[75] Inventors: Shoichi Chokai, Kyoto; Yojiro Ukai, Shiga; Tomiyoshi Aoki, Shiga; Kyoichi Ideguchi, Shiga, all of Japan

[73] Assignee: Nippon Shinyaku Co., Ltd., Kyoto, Japan

[21] Appl. No.: 08/809,004

[22] PCT Filed: Sep. 8, 1995

[86] PCT No.: PCT/JP95/01792

§ 371 Date: Mar. 7, 1997

§ 102(e) Date: Mar. 7, 1997

[87] PCT Pub. No.: WO96/07641

PCT Pub. Date: Mar. 14, 1996

[30] Foreign Application Priority Data

Sep. 9, 1994 [JP] Japan .................................. 6/216214

[51] Int. Cl.$^6$ .......................... A01N 43/54; C07D 239/02
[52] U.S. Cl. .......................... 514/269; 514/272; 544/319; 544/321
[58] Field of Search .................. 544/319, 321; 514/269, 272

[56] References Cited

U.S. PATENT DOCUMENTS

| | | | |
|---|---|---|---|
| 4,698,340 | 10/1987 | Takaya et al. | 514/222 |
| 4,727,073 | 2/1988 | Takaya et al. | 514/252 |
| 5,589,477 | 12/1996 | Chokai et al. | 514/256 |

FOREIGN PATENT DOCUMENTS 0 177 287 A2  9/1985  European Pat. Off. .

OTHER PUBLICATIONS

Brown et al, Chemical Abs., vol. 100, (1984) Abs# 209733u, p. 589.
Barlin et. al., Chemical Abs., vol. 106, (1987), Abs# 18488g, p. 601.
Wintersteiger et. al., "Über 4–Alkylamino . . . ", Sci. Pharm., vol. 48, (1980), pp. 68–78.

*Primary Examiner*—Mukund J. Shah
*Assistant Examiner*—Tamthom N. Truong
*Attorney, Agent, or Firm*—Graham & James LLP

[57] ABSTRACT

A pharmaceutical composition comprising a compound of the following general formula [I] or its salt.

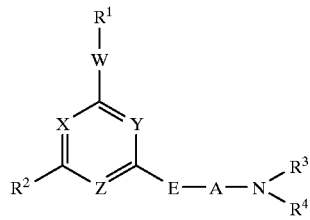

wherein $R^1$ represents aryl or a heteroaromatic group.

$R^2$ represents hydrogen, alkyl, alkenyl, cycloalkyl, cycloalkylalkyl, hydroxyalkyl, haloalkyl, alkoxy, alkylthio, amino, monoalkylamino, dialkylamino, or phenyl. $R^3$ and $R^4$ independently represent hydrogen or alkyl or $R^3$ and $R^4$ taken together with the adjacent N atom represent a 5- through 7-membered cyclic amino group. A represents $C_{2-10}$ alkylene. W represents O, S, or $(CH)_n$ (where CH may be substituted by alkyl; n is an integer of 1 or 2). X, Y, and Z may be the same or different and each represents CH (which may be substituted by alkyl), or N. Provided, however, that the case in which X, Y, and Z concurrently represent CH is excluded. The compound of the invention has excellent neuronal death inhibitory activity and is useful as a therapeutic drug for cerebrovascular diseases.

16 Claims, No Drawings

DERIVATIVES OF PYRIMIDINE FOR TREATING ACUTE CEREBROVASCULAR DISORDERS

This is a 371 application of PCT/JP95/01792, filed on Sep. 8, 1995.

TECHNICAL FIELD

The present invention relates to a heterocyclic derivative which is useful as a medicine.

BACKGROUND ART

Cerebrovascular disease is a condition in which the blood vessels circulating the brain are impaired by, for example, cerebral infarction, cerebral hemorrhage, head trauma, or subarachnoid hemorrage. As the flow of blood to the brain is interrupted or decreased by a cerebrovascular disease and the brain becomes ischemic, the nerve cells are damaged. Even if the patient narrowly escapes death, he or she suffers from sequelae of neuronal death caused by this impairment. Therapeutic agents for cerebrovascular disease may be classified into the agents which act against brain infarction, hemorrhage, etc. and those which inhibit said neuronal death.

It has recently become clear that once the brain tissue is brought into an ischemic state, even if the ischemia is transiently and the complete recovery of regional blood flow reinstates the normal energy metabolism and neural activity once, the final outcome is death of nerve cells. Such pathological changes of nerve cells, which characteristically occur predominantly in the hippocampus, manifest themselves in 3–4 days after ischemia and, therefore, are called delayed neuronal death. Moreover, even in the cerebral region not exposed to reperfusion, there are domains in which the blood flow is not completely interrupted but decreased. It is said that the nerve cells in such domains also succumb to death on prolongation of ischemia. This death of nerve cells could be blocked, the sequelae of a cerebrovascular disease following ischemia could be prevented.

It is known that the cerebral metabolism enhancer, propentofylline is effective against delayed neuronal death but, partly because of its side effects, is not a fully satisfactory medicine.

With therapeutic drugs in this field being the target, much research has been undertaken into inhibitors of excitatory amino acids. This is predicated on the concept of preventing ischemic death of neurons by inhibiting the excessive excitation of neurons following brain ischemia. It is well known that glutamic acid or glutamate is such an excitatory amino acid. As inhibitors of the excitatory amino acid, many glutamate antagonists which would specifically block the receptors of this amino acid and compounds which inhibit the release of glutamate are already known. The glutamate receptors are classified into the N-methyl-D-aspartate (hereinafter referred to as NMDA) receptors and receptors other than said NMDA receptors (hereinafter referred to as non-NMDA receptors). As an NMDA antagonist, MK-801, for instance, is known, while YM-90K, for instance, is known to be a non-NMDA antagonist. As glutamate release inhibitors, 2,4-diamino-5-(2,3,5-trichlorophenyl)pyrimidine and 2,4-diamino-5-(2-chlorophenyl)pyrimidine are known [EP-A 459830; 6th SCI-RSC Medical Chemistry Symposium, Sep. 8–11, 1991].

Meanwhile, it is described in WO 92/04333 that a phenylpyrimidine derivative has learning-and-memory disorder improving activity and finds application in dementia. While various nerve systems have been impaired in dementia, it is known that the impairment of the cholinergic nervous system playing an important role in learning-and-memory is particularly serious. The phenylpyrimidine derivative disclosed in WO 92/04333 acts on the cholinergic nervous system and activates the residual nerve cells to ameliorate the learning-and-memory defects. This learning-and-memory improving action is quite different from the action to inhibit the onset of sequelae of a cerebrovascular disease through inhibition of neuronal death.

In addition to the above-mentioned compounds, a variety of pyrimidine derivatives have so far been reported. For example, Japanese Examined Publication S48-21949 discloses that 4-methyl-2-phenyl-6-[2-(4-phenylpiperazin-1-yl)ethyloxy]pyrimidine, among others, has α-sympatholytic activity (sedation, hypotension, and vasodilation). Moreover, it is reported in CA 100: 209733u and CA 106: 18488r that 4-[2-(N,N-dimthylamino)ethyloxy]-6-methyl(or phenyl)-2-phenylpyrimidine and 4-[2-(N,N-dimethylamino) ethylthio]-6-methyl(or phenyl)-2-phenylpyrimidine respectively have the property to amplify the action of phleomycin. Furthermore, it is reported in J. Med. Chem. 31(6), 1231–40 (1988) that 2-(2-dimethylamino)ethylthio-4-methyl(or unsubstituted)-6-phenyl(or aromatic heterocyclyl) pyrimidine derivatives and 2-[2-(N,N-dimethylamino) ethoxy]-4-thienylpyrimidine derivatives amplify the action of bleomycin.

DISCLOSURE OF INVENTION

The present invention has for its object to provide a pharmaceutical composition having a neuronal death inhibitory action and a novel heterocyclic compound which is an active ingredient of said composition.

To accomplish the above-mentioned object, the inventors of the present invention have synthesized and screened a variety of compounds. In the course, they have discovered that a compound of the following general formula [I] has a protetive activity aginst neuronal death, which is quite different from said learning-and-memory disorder improving action, with low toxicity, and have perfected the present invention. The compound of the present invention exhibits an excellent protective activity against neuronal death particularly in the acute phase of a cerebrovascular disorder and is, therefore, useful for the therapy of a cerebrovasuclar disorder and the inhibition of the onset of its sequelae.

The present invention, in one aspect, relates to a pharmaceutical composition comprising a compound of the following general formula or a salt thereof, or a solvate thereof, as an active ingredient.

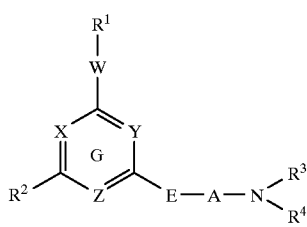

[I]

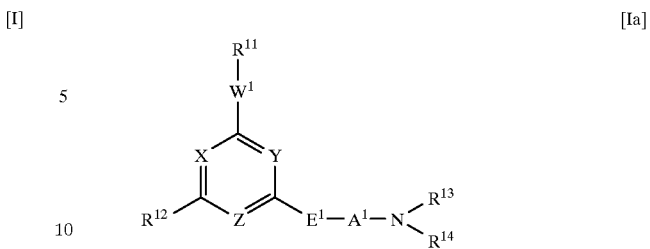

[Ia]

wherein $R^1$ represents an aryl group that may be substituted or a 5- through 10-membered heteroaromatic group that may be substituted. The heteroaromatic group mentioned above is a monocyclic or fused ring system containing at least one hetero-atom selected from the group consisting of nitrogen, oxygen, and sulfur as a ring member. Each of said aryl group and heteroaromatic group may be substituted by 1–3 substitutes, whether the same or different, as selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro.

$R^2$ represents hydrogen, alkyl, alkenyl, cycloalkyl, cycloalkylalkyl, hydroxyalkyl, haloalkyl, alkoxy, alkylthio, amino, monoalkylamino, dialkylamino, or phenyl that may be substituted. The phenyl mentioned just above may be substituted by 1–3 same or different substitutes selected from the group consisting of halogen, alkyl, and alkoxy.

$R^3$ and $R^4$ may be the same or different and each represents hydrogen or alkyl that may be substituted (this alkyl may be substituted by 1 or 2 same or different substitutes selected from the group consisting of hydroxy, alkoxy, amino, monoalkylamino, and dialkylamino), or $R^3$ and $R^4$ taken together with the adjacent N atom represent a 4- through 8-membered cyclic amino group of the formula $NR^3R^4$. This cyclic amino group may contain N, O, or S in addition to said N atom as a ring member and may be substituted by 1–3 substitutes, whether the same or different, as selected from the group consisting of alkyl, alkoxy, hydroxy, oxo, amino, monoalkylamino, dialkylamino, aryl that may be substituted, and pyridyl.

The N atom to which $R^3$ and $R^4$ are bound may form an oxide.

The symbol A represents alkylene of 2–10 carbon atoms. The alkylene may be substituted by one or more substitutes selected from the group consisting of alkoxy, hydroxy, and oxo in optional substitutable positions.

E represents O or S.

W represents a single bond, O, S, or $(CH_2)_n$ (where $CH_2$ may be substituted by alkyl; n is an integer of 1 or 2).

X, Y, and Z may be the same or different and each represents CH, CR (where R represents alkyl), or N. Excluded, however, is the case in which X, Y, and Z concurrently represent carbon, i.e. CH or CR.

Ring G represents pyridine, pyrimidine, or 1,3,5-triazine.

When any one through all the three of X, Y, and Z represent N, one of them may form an oxide.

The present invention, in another aspect, relates to a compound of the following general formula [Ia] and a salt thereof, inclusive of a solvate thereof.

wherein $R^{11}$, $R^{12}$, $R^{13}$, $R^{14}$, $A^1$, $E^1$, $W^1$, $X^1$, $Y^1$, and $Z^1$ correspond to $R^1$, $R^2$, $R^3$, $R^4$, A, E, W, X, Y, and Z, respectively, in formula [I];

Provided, however, that the following compounds are excluded.

(a) The compound in which $A^1$ is an alkylene group of 2–3 carbon atoms, $X^1=Y^1=N$ with $Z^1=CH$ or $X^1=Z^1=N$ with $Y^1=CH$, $W^1$ is a single bond, $E^1$ is O, $R^{11}$ is phenyl that may be substituted by hydroxy, alkoxy, trifluoromethyl, or halogen, $R^{12}$ is methyl, trifluoromethyl, or tert-butyl.

(b) The compound in which $A^1$ is an alkylene group of 2 carbon atoms, $X^1=Y^1=N$ with $Z^1=CH$, $W^1$ is $—(CH_2)_2—$, $E^1$ is O, $R^{11}$ is phenyl, and $R^{22}$ is methyl.

(c) The compound in which $A^1$ is an alkylene group of 2 carbon atoms, ring G is pyrimidine, $W^1$ is a single bond, $E^1$ is S, and $R^{12}$ is hydrogen, methyl, or phenyl.

One of the features of the present invention is that the compound of formula [I] has brain neuronal death (death of nerve cells) protective activity which is quite different from the learning-and-memory disturbance ameliorating activity of the known phenylpyrimidine derivative (WO 92/04333) which is structurally analogous to the compound of the invention or from the α-sympatholytic activity of the piperazine derivative described in JP Examined Publication S48-21949.

The structural characteristics of the compound [Ia] of the present invention are as follows: (1) the compound is structurally remote from the known therapeutic agents for cerebrovascular disease which are predicated either on glutamate antagonist-like activity or on glutamate release inhibitory activity and (2) the compound is different from the phenylpyrimidine derivative disclosed in WO 92/04333 in the number of carbon atoms constituting the alkylene chain.

Among species of the compound of general formula [I], the above compound categories (a)–(c) include known species. However, the present inventors should be credited with the first discovery of excellent neuronal death inhibitory activity in these compounds.

As examples of the compound of general formula [I], species of the following compound categories (A)–(D) can be mentioned.

(A) The compound in which $NR^3R^4$ is a 4- through 8-membered cyclic amino group and A is an alkylene group of 4–10 carbon atoms. The cyclic amino group may have oxygen or sulfur as a ring member and may have alkyl, alkoxy, hydroxy, oxo, amino, monoalkylamino, dialkylamino, pyridyl, or aryl as a substituent. The aryl mentioned just above may be substituted by 1–3 same or different substitutes selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro.

(B) The compound in which, referring to general formula [I], $R^1$ is a 5- through 10-membered heteroaromatic group, $R^2$ is hydrogen, A is an alkylene group of 2–3 carbon atoms, which may be substituted by alkoxy, hydroxy, or oxo in an optional substitutable position, and E is O. The heteroaromatic group mentioned above is a monocyclic or fused ring system containing at least one hetero-atom selected from the group consisting of nitrogen, oxygen, and sulfur as a ring constituent atom and may be substituted by 1–3 same or different substitutes selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro.

(C) The compound in which $R^1$ is a 5- through 10-membered membered heteroaromatic group which may be a monocyclic or fused ring system containing at least one hetero-atom selected from the group consisting of nitrogen, oxygen, and sulfur as a ring constituent atom, said heteroaromatic group being optionally substituted by 1–3 same or different substitutes selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro; $R^2$ is alkyl, alkenyl, cycloalkyl, cycloalkylalkyl, hydroxyalkyl, haloalkyl, alkoxy, alkylthio, amino, monoalkylamino, dialkylamino, or phenyl; said phenyl may be substituted by 1–3 same or different substitutes selected from the group consisting of halogen, alkyl, and alkoxy; and A is an alkylene group of 2–3 carbon atoms, which may be substituted by alkoxy, hydroxy, or oxo in an optional substitutable position.

(D) The compound in which $R^1$ is a 5- through 10-membered heteroaromatic group which may be a monocyclic or fused ring system which may contain at least one hetero-atom the group consisting of nitrogen, oxygen and sulfur as a ring constituent atom and be optionally substituted by 1–3 same or different substitutes selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro; $NR^3R^4$ is piperazino which may be unsubstituted or substituted by alkyl, alkoxy, hydroxy, oxo, amino, monoalkylamino, dialkylamino, pyridyl, or aryl, said aryl being optionally substituted by 1–3 same or different substitutes selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkyl-amino, dialkylamino, carboxy, alkoxycarbonyl, cyano, and nitro.

As used throughout this specification, the term "alkyl" means a straight-chain or branched alkyl group of 1–6 carbon atoms, such as methyl, ethyl, n-propyl, isopropyl, n-butyl, isobutyl, sec-butyl, tert-butyl, n-pentyl, isopentyl, n-hexyl, or isohexyl. Particularly preferred is an alkyl group of 1–4 carbon atoms.

The alkenyl means a group of 2–6 carbon atoms, such as vinyl, allyl, 3-butenyl, 2-pentenyl, or 4-hexenyl.

The cycloalkyl is preferably a group of 3–10 carbon atoms, such as cyclopropyl, cyclobutyl, cyclopentyl, cyclohexyl, cycloheptyl, cyclooctyl, 1-adamantyl, or 2-adamantyl.

The aryl means a group of 6–13 carbon atoms, such as phenyl, 1-naphthyl, 2-naphthyl, or biphenyl. Particularly preferred is phenyl.

The aralkyl means a group of 7–13 carbon atoms, whose alkyl moiety is either straight-chain or branched, thus including benzyl, phenethyl, phenylpropyl, phenylbutyl, diphenylmethyl, and naphthylmethyl, among others.

The halogen includes chlorine, fluorine, bromine, and iodine.

The alkoxy is preferably a straight-chain or branched group of 1–6 carbon atoms, such as methoxy, ethoxy, n-propoxy, isopropoxy, n-butoxy, isobutoxy, sec-butoxy, tert-butoxy, n-pentyloxy, isopentyloxy, n-hexyloxy, or isohexyloxy.

The alkanoyl means a straight-chain or branched group of 1–6 carbon atoms, such as acetyl, propanoyl, butanoyl, isobutanoyl, pentanoyl, hexanoyl, or 2-methylpentanoyl.

The alkylthio is preferably a group having a straight-chain or branched alkyl moiety of 1–6 carbon atoms, such as methylthio, ethylthio, n-propylthio, isopropylthio, n-butylthio, isobutylthio, sec-butylthio, tert-butylthio, n-pentylthio, isopentylthio, n-hexylthio, or isohexylthio.

The alkylsulfonyl is preferably a group having a straight-chain or branched alkyl moiety of 1–6 carbon atoms, such as methylsulfonyl, ethylsulfonyl, n-propylpentylsulfonyl, isopropylsulfonyl, n-butylsulfonyl, isobutyl- sulfonyl, sec-butylsulfonyl, tert-butylsulfonyl, n-pentylsulfonyl, isopentylsulfonyl, n-hexylsulfonyl, or isohexylsulfonyl.

The hydroxyalkyl is a group having a straight-chain or branched alkyl moiety of 1–6 carbon atoms, such as 2-hydroxyethyl, 3-hydroxypropyl, 2-hydroxy-propyl, 4-hydroxybutyl, 3-hydroxybutyl, 5-hydroxypentyl, or 6-hydroxyhexyl.

The haloalkyl is a group having a straight-chain or branched alkyl moiety of 1–6 carbon atoms, such as trifluoromethyl, fluoromethyl, 2-bromoethyl, or 3-chloroethyl.

The monoalkylamino is a group having a straight-chain or branched alkyl moiety of 1–6 carbon atoms, such as methylamino, ethylamino, propylamino, butylamino, heptylamino, or hexylamino.

The dialkylamino is a group having straight-chain or branched alkyl moieties of 1–6 carbon atoms, such as dimethylamino, diethylamino, dipropylamino, dibutylamino, diheptylamino, or dihexylamino.

The alkoxycarbonyl is preferably a straight-chain or branched group of 2–7 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, n-hexyloxycarbonyl, or isohexyloxycarbonyl.

The cycloalkyloxy is preferably a group of 3–10 carbon atoms, such as cyclopropyloxy, cyclobutyloxy, cyclopentyloxy, cyclohexyloxy, cycloheptyloxy, cyclooctyloxy, or 2-adamantyloxy.

The cycloalkylalkyl is preferably a group of 4–11 carbon atoms, such as cyclopropylmethyl, cyclopropylethyl, cyclobutylmethyl, cyclobutylethyl, cyclopentylmethyl, cyclopentylethyl, cyclopentylpropyl, cyclohexylmethyl, cyclohexylethyl, cyclohexylpropyl, cycloheptylmethyl, or 2-adamantylmethyl.

The 4- through 8-membered cyclic amino group includes azetidin-1-yl, pyrrolidin-1-yl, piperidino, hexamethylenimino, tetrahydropyridino, octahydroazocin-1-yl, piperazin-1-yl, homopiperazin-1-yl, morpholino, and thiomorpholino.

The substituent that may be present on said cyclic amino group includes alkyl, alkoxy, hydroxy, oxo, amino, monoalkylamino, dialkylamino, aryl that may be substituted, and pyridyl that may be substituted. The substituent that may be present on the aryl or pyridyl includes the groups mentioned for the substituent on $R^1$.

The 5- through 10-membered heteroaromatic group is a monocyclic or fused ring system, which contains not less than 1 hetero-atom selected from the group consisting of oxygen, sulfur and nitrogen. Thus, for example, 2-pyridyl, 3-pyridyl, 4-pyridyl, 2-thienyl, 2-furyl, 2-pyrimidinyl, 4-pyrimidinyl, 5-pyrimidinyl, 3-pyridazinyl, 4-pyridazinyl, 1-isoquinolyl, 4-isoquinolyl, 2-quinazolinyl and 1-methyl-2-indolyl can be mentioned.

The alkylene represented by A may be straight-chain or branched. For use of the compound as a therapeutic drug for cerebrovascular disease, A is preferably an alkylene group of 3–6 carbon atoms and more preferably a group of 4–6 carbon atoms. As far as the chemical compound is concerned, $A^1$ is preferably an alkylene group of 4–6 carbon atoms.

E preferably represents O.

W preferably represents a single bond.

X, Y, and Z are preferably such that X=Z=N with Y=CH or Z=N with X=Y=CH. The former combination is particularly preferred.

$R^1$ preferably represents halogen-substituted phenyl, particularly fluorophenyl.

$R^2$ is preferably alkyl or haloalkyl and more preferably alkyl. Particularly preferred is methyl.

Preferably, $R^3$ and $R^4$ taken together with the adjacent N atom represent a cyclic amino group of the formula —NR³R⁴. In particular, a cyclic amino group containing only one nitrogen atom as a ring-constituent hetero-atom is preferred. Especially preferred is piperidino.

The compound which is particularly preferred in the sense that the delayed neuronal death can be inhibited regardless of whether it is administered before the onset of brain ischemia or after the onset is the compound of formula [Ib].

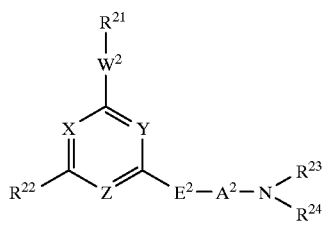

In the formula, $A^{21}$ represents an alkylene group of 4–6 carbon atoms.

$E^{21}$ represents O.

$X^{21}=Z^{21}=N$ with $Y^{21}=CH$, or $X^{21}=Y^{21}=CH$ with $Z^{21}=N$.

$R^{21}$ represents halogen-substituted phenyl.

$R^{22}$ represents alkyl or haloalkyl.

$R^{23}$ and $R^{24}$ taken together with the adjacent N atom represent a 4 through 8 membered cyclic amino group of the formula —NR²³R²⁴, said cyclic amino group containing only one nitrogen atom as a ring constituent hetero-atom.

As particularly preferred species of the above compoud, there can be mentioned 4-(4-fluorophenyl)-2-methyl-6-(4-piperidinobutoxy)pyrimidine, 4-(4-fluorophenyl)-2-methyl-6-(1-methyl-4-piperidinobutoxy)pyrimidine, 4-(4-fluorophenyl)-2-methyl-6-(5-piperidinopentyloxy) pyrimidine, 4-(4-fluorophenyl)-2-methyl-6-(6-piperidinohexyloxy)pyrimidine, 2-(4-fluorophenyl)-4-methyl-6-(4-piperidinobutoxy)pyrimidine, 4-(4-fluorophenyl)-2-methyl-6-(3-piperidinopropoxy)pyridine, and 4-(4-fluorophenyl)-2-methyl-6-(5-piperidinopentyloxy) pyridine, inclusive of their salts.

The solvate of compound [I] falling within the scope of the present invention includes the hydrate and solvate with ethanol.

The salt of compound [I] falling within the scope of the invention includes salts with mineral acids such as hydrochloric acid, sulfuric acid, nitric acid, phosphoric acid, hydrofluoric acid and hydrobromic acid, and salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The compound of formula [I] according to the present invention can be produced by, for example, the following processes.

Process A

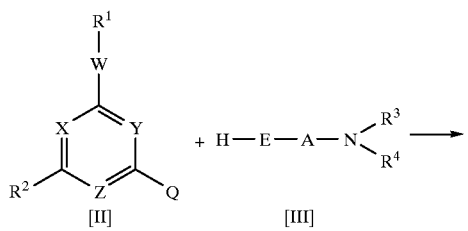

-continued

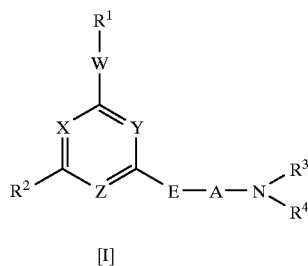

[I]

In the above reaction schema, $R^1$–$R^4$, A, E, X, Y, Z, and W are as defined hereinbefore. Q represents halogen, preferably chlorine.

The compound [Ia] of the invention can be synthesized by reacting halide [II] with compound [III] in the presence of a base in a solvent inert to the reaction. The reaction solvent that can be used includes aprotic polar solvents such as N,N-dimethylformamide (DMF), aromatic hydrocarbons such as benzene, toluene and xylene, hydrocarbons such as n-hexane, n-heptane and cyclohexane, and ethers such as tetrahydrofuran, dimethoxyethane, diethyl ether, dioxane and diethylene glycol dimethyl ether, inclusive of mixtures of such solvents. The base that can be used includes sodium hydride, sodium amide, potassium tert-butoxide, butyllithium, and so on. This reaction is conducted generally at 0–140° C. and preferably at 10–110° C. Dependent on the species of reactants, solvent, and base, a reaction time of 2–24 hours is generally appropriate. The preferred proportions of compound [III] and said base are generally 1–1.2 moles per mole of compound [II].

Process B

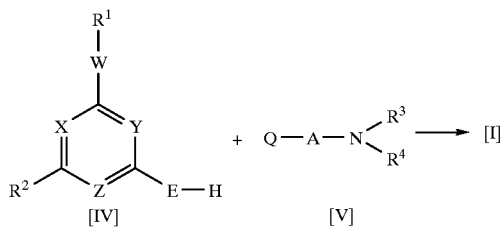

In the above reaction schema, $R^1$–$R^4$, A, E, X, Y, Z, W, and Q are as defined hereinbefore.

The compound of formula [Ia] can be synthesized by reacting compound [IV] with halide [V] in the presence of a base in a solvent inert to the reaction at 0–80° C. The reaction solvent that can be used includes aprotic polar solvents such as acetonitrile, dimethyl sulfoxide, and N,N-dimethylformamide (DMF), alcohols such as methanol, ethanol and isopropyl alcohol, ethers such as tetrahydrofuran, dimethoxyethane, diethyl ether and dioxane, glymes such as methylcellosolve and ethylene glycol dimethyl ether, halogenated hydrocarbons such as methylene chloride and chloroform, aromatic hydrocarbons such as benzene, toluene and xylene, and mixtures of such solvents. The base that can be used includes sodium hydride, potassium carbonate, sodium hydroxide, potassium hydroxide, silver carbonate and the like. Dependent on the species of reactants, base, and solvent, the reaction time may generally range from 2 to 10 hours. The preferred proportions of halide [V] and said base are generally 1–1.2 moles per mole of compound [IV].

Process C

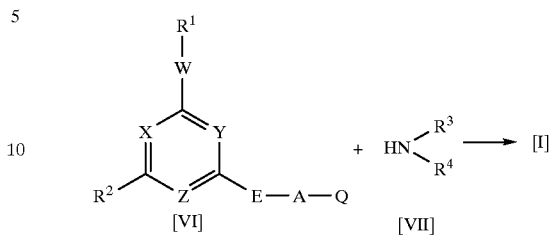

In the above reaction schema, $R^1$–$R^4$, A, E, X, Y, Z. W, and Q are as defined hereinbefore.

Compound [Ia] can be synthesized by reacting halide [VI] with amine [VII] in the presence of a base in a solvent inert to the reaction. The reaction solvent that can be used includes aprotic polar solvents such as acetonitrile, dimethyl sulfoxide, N,N-dimethylformamide (DMF) and acetone, ethers such as tetrahydrofuran, dimethoxyethane, diethyl ether and dioxane, aromatic hydrocarbons such as benzene, toluene, xylene, etc., and mixtures of such solvents. The base that can be used includes alkali metal salts such as potassium carbonate, sodium carbonate, sodium hydrogen carbonate, sodium hydroxide, and potassium hydroxide. In lieu of such a base, the amine [VII] may be used in excess. This reaction is conducted at 10–100° C. Depending on the species of reactants, base, and solvent used, the reaction time may generally range from 2 to 20 hours. The preferred proportion of compound [VII] is generally 1–3 moles per mole of compound [VI]. The preferred proportion of the base is generally 1–1.2 moles per mole of compound [VI].

Process D (Compound in which A represents an alkylene group of 3–10 carbon atoms and which have hydroxy, oxo, or alkoxy in the β-position of $NR^3R^4$)

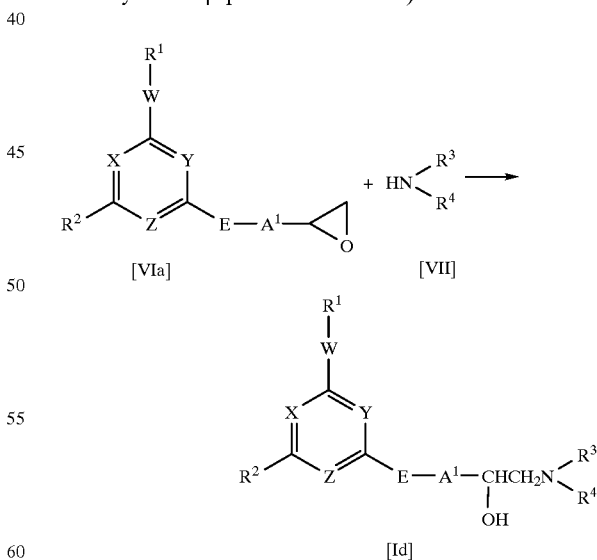

In the above reaction schema, $R^1$–$R^4$, E, W, X, Y, Z, and Q are as defined hereinbefore. $A^0$ represents an alkylene group of 1–8 carbon atoms which may be substituted.

Compound [Id] having hydroxy in the β-position of $NR^3R^4$ according to the invention can be synthesized by conducting the reaction according to Process C using epoxy compound [VI$^a$] in lieu of halide [VI]. This reaction proceeds in the absence of a base. The proportion of the amine varies with its species but is generally equimolar or excess relative to compound [VI$^a$].

By oxidizing the above compound [Id] in a solvent inert to the reaction (e.g. DMSO/acetic anhydride) using an oxidizing agent such as chromic acid, manganese dioxide, or potassium permanganate in the per se known manner, the compound having oxo in the above-mentioned position can be obtained.

Moreover, by reacting compound [Id] with an alkyl halide in the presence of a base such as sodium hydride, or butyllithium in a solvent inert to the reaction, the compound having alkoxy in the same position can be obtained.

Process E (the compound of formula [I] in which W represents O or S]

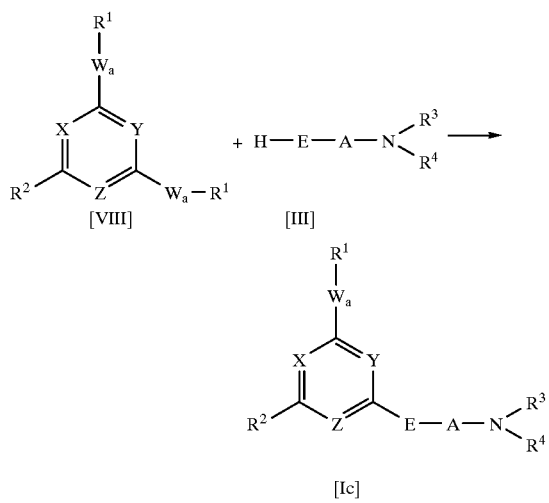

In the above reaction schema, $R^1$–$R^4$, A, E, X, Y, Z, and Q are as defined hereinbefore. Wa represents O or S.

Compound [Ic] in which W is O or S, which belongs to the compound of the present invention, can be synthesized by reacting compound [VIII] with compound [III] in the presence of a base in a solvent inert to the reaction. The reaction solvent that can be used includes aprotic polar solvents such as N,N-dimethylformamide (DMF), ethers such as tetrahydrofuran, dimethoxyethane, diethyl ether and dioxane, and mixtures of such solvents. The base that can be used includes sodium hydride, sodium amide, potassium tert-butoxide, butyllithium and the like.

The reaction is carried out at 0–80° C., preferably 10–30° C. Depending on the species of reactants, base, and solvent, the reaction goes to completion generally in 2–24 hours. The proportions of compound [VIII] and compound [III] used are preferably equimolar. The preferred proportion of the base is generally 1–1.2 moles per mole of compound [VIII].

In case the objective compound is a compound [I] having an amino group or a hydroxyl group, it can be obtained by protecting the starting compound with a leaving group beforehand as necessary, carrying out the reaction according to any of the above processes A through E, and removing the protective group in the per se known manner. The amino-protecting group that can be used includes but is not limited to benzyl, benzyloxycarbonyl, trifluoroacetyl, and t-butoxycarbonyl. The hydroxy-protecting group that can be used includes but is not limited to methoxymethyl, 2-methoxyethoxymethyl, methylthiomethyl, tetrahydropyranyl, t-butyl, benzyl, trimethylsilyl, and t-butyldimethylsilyl. By way of illustration, the compound having a phenolic hydroxyl group according to the invention can be obtained by using a starting compound protected with benzyl beforehand and, after the reaction, removing the protective group by catalytic reduction. Such catalytic reduction is generally carried out under atmospheric to under pressure in a solvent at 0–80° C. The solvent that can be used includes alcohols, e.g. methanol, ethanol, etc., water, carboxylic acids such as acetic acid etc., esters such as ethyl acetate, and ethers such as dioxane and tetrahydrofuran. The catalyst that can be used includes palladium-on-carbon, palladium black, platinum oxide, and the like. Depending on the species of the starting compound, catalyst, and solvent used, the preferred reaction time is generally 30 minutes to 48 hours.

The starting compounds [II] and [IV] can be produced by the known method [WO 92/04333] as will be described hereinafter as reference examples.

The starting compound [VI] can be produced according to the following reaction schema.

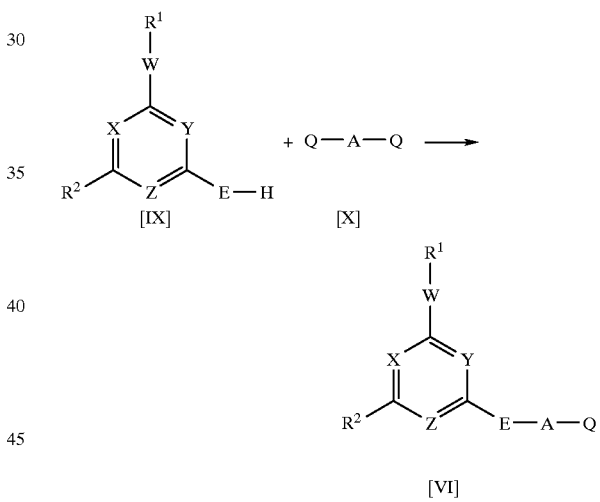

In the above schema, $R^1$–$R^2$, A, E, X, Y, Z, W, and Q are as defined hereinbefore.

Compound [VI] can be synthesized by reacting compound [IX] with halide [X] in the presence of a base in a solvent inert to the reaction. The reaction solvent that can be used includes aprotic polar solvents such as acetonitrile, dimethyl sulfoxide, and N,N-dimethylformamide (DMF), ethers such as tetrahydrofuran, dimethoxyethane, diethyl ether and dioxane, aromatic hydrocarbons such as benzene, toluene, and xylene, and mixtures of such solvents. The base that can be used includes silver carbonate, potassium carbonate, sodium carbonate, sodium hydride, sodium hydroxide, and potassium hydroxide. The reaction is conducted at 20–160° C., preferably 70–120° C. Depending on the kinds of reactants, base, and solvent used, the reaction time may appropriately be 5–60 hours. The preferred proportion of halide [X] is generally 1–4 moles per mole of compound

[IX]. The preferred proportion of the base is 0.5–1.2 moles per mole of compound [IX].

The starting epoxy compound [VI$^a$] can be produced according to the following reaction schema.

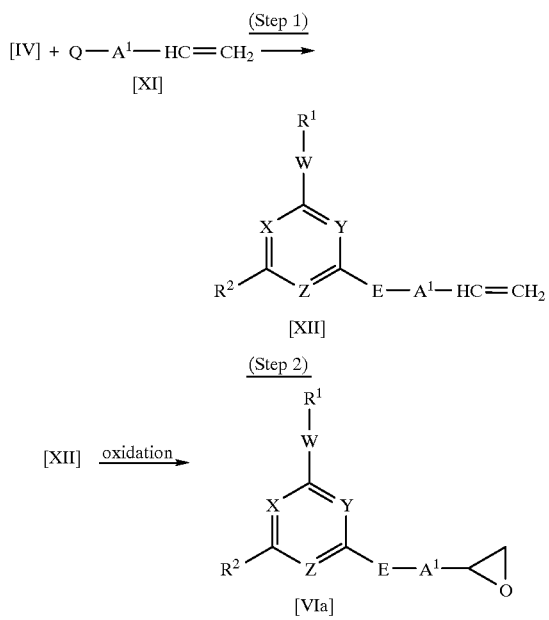

In the above reaction schema, R$^1$–R$^2$, A$^0$, E, X, Y, Z, W, and Q are as defined hereinbefore.

(Step 1)

Compound [XII] can be synthesized by reacting compound [IV] with halide [XI] in the presence of a base in a solvent inert to the reaction. This reaction can be conducted under the same conditions as the above-mentioned process for producing [VI]. The preferred proportion of halide [XI] is generally 1–3 moles per mole of compound [IV].

(Step 2)

Epoxy compound [VI$^a$] can be synthesized by oxidizing compound [XII] with a suitable oxidizing agent in a solvent inert to the reaction. The reaction solvent that can be used includes halogenated hydrocarbons such as dichloromethane, dichloroethane and chloroform, ethers such as tetrahydrofuran, dimethoxyethane, diethyl ether and dioxane, aromatic hydrocarbons such as benzene, toluene and xylene, and mixtures of such solvents. The oxidizing agent that can be used includes but is not limited to organic peracids such as perbenzoic acid, m-chloroperbenzoic acid, peracetic acid and monoperoxyphthalic acid; hydrogen peroxide; and t-butyl hydroperoxide. The amount of the oxidizing agent varies with its species but is preferably 1–2 moles per mole of compound [XII]. This reaction is conducted at 0–50° C., preferably 10–30° C. Depending on the species of the starting compound, oxidizing agent, and solvent used, the reaction time may generally range from 2 to 24 hours.

The starting compound [VIII] can be produced in accordance with the following reaction schema.

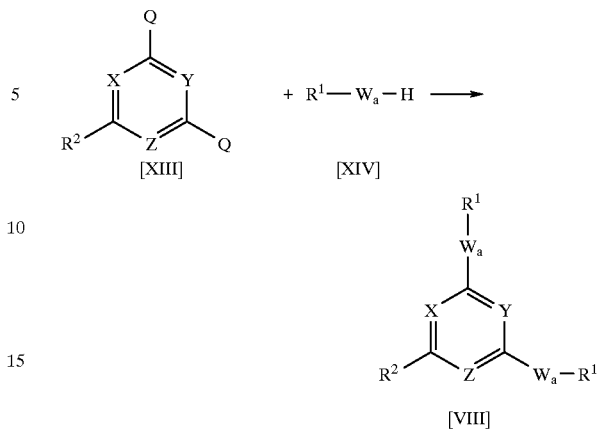

In the reaction schema, R$^1$, R$^2$, X, Y, Z, Wa, and Q are as defined hereinbefore.

Compound [VIII] can be synthesized by reacting halide [XIII] with compound [XIV] in the presence of a base in a solvent inert to the reaction. This reaction can be carried out under the same conditions as the above-mentioned reaction for producing [Ia].

The preferred proportion of compound [XIV] is 2–2.5 moles per mole of halide [XIII].

The compound [I] of the present invention can be treated with a peracid in the per se known manner to provide the oxide.

While some species of the compound of the invention contain asymmetric carbon, the respective optical isomers as well as the racemic mixtures also fall within the scope of the invention. Thus, the racemic compound synthesized by any of the above-mentioned processes can be fractionated into the optical isomers by the conventional optical resolution technique utilizing its basicity, i.e. with a chiral acid (e.g. tartaric acid, dibenzoyltartaric acid, mandelic acid, 10-camphorsulfonic acid), or such optical isomers can be respectively synthesized by using an optically active compound prepared beforehand (e.g. 1,2-epoxypropane) as a starting material.

The compound [I] of the present invention can be converted to the salts mentioned hereinbefore in a well known manner. For example, the hydrochloride of compound [I] can be obtained by dissolving compound [I] in an alcoholic solution of hydrogen chloride.

Among species of compound [I] according to the present invention, any compound containing a carboxyl group can be converted to the corresponding salt by the known process. The salt here includes alkali metal salts such as sodium salt and potassium salt, and alkaline earth metal salts such as calcium salt. For instance, an alkali metal salt of compound [I] of the invention can be produced by adding one equivalent of sodium hydroxide, potassium hydroxide, or the like to a carboxy-containing compound [I] of the invention, preferably in an alcoholic solvent. An alkaline earth metal salt of compound [I] of the invention can be produced by dissolving the above alkali metal salt in water, methanol, or ethanol, or a mixture thereof, for instance, and adding one equivalent of, for example, calcium chloride.

The solvate (inclusive of the hydrate) of the compound [I] or salt of the invention is also included in the scope of the present invention. The solvate can be generally produced by recrystallizing the compound from the corresponding solvent or a suitable mixed solvent containing example, corresponding solvent. For example, the hydrate of compound [I] of the present invention can be obtained by recrystallizing compound [I] from an aqueous alcohol.

Compound [I] of the present invention may show crystal polymorphism. The polymorphs in such cases are also included in the scope of the invention.

The object compound [I] thus obtained can be isolated and purified in the form of the free base or an acid addition salt by per se known procedures such as concentration, pH adjustment, phase transfer, solvent extraction, crystallization, fractional distillation, and chromatography.

The compound of the present invention is useful as a therapeutic drug for cerebrovascular disease or as a drug for inhibiting onset of sequelae of cerebrovascular disease.

For use as a medicine, the compound of the present invention can be administered to an animal including human being either as it is or in the form of a pharmaceutical composition containing, for example, 0.01–99.5%, preferably 0.5–90%, of the compound in a pharmaceutically acceptable nontoxic, inert carrier.

As the carrier, one or more of solid, semisolid, or liquid diluent, filler, and other formulation auxiliaries can be employed. The pharmaceutical composition is preferably administered in unit dosage forms. The pharmaceutical composition of the present invention can be administered orally, parenterally (e.g. intravenously), locally (e.g. transdermally), or rectally. Of course, dosage forms suited for respective routes of administration should be selected. Particularly preferred is intravenous or oral administration.

The dosage as a therapeutic drug for cerebrovascular disease is preferably established with reference to the patient's age, body weight and other factors, route of administration, nature and severity of illness, etc. Usually, however, the daily oral dosage for human adults may range generally from 0.1 mg to 1 g/patient and preferably from 1 to 300 mg/patient. In the case of intravenous administration, the usual daily dose is 0.01 mg–100 mg/patient and preferably 0.1–30 mg/patient. Lower dose levels may be sufficient in some cases, while higher doses may be necessary in other cases. The above-mentioned dosage can be preferably administered in 2–4 divided doses.

Oral administration can be carried out using solid or liquid unit dosage forms such as bulc powders, powders, tablets, dragees, capsules, granules, suspensions, solutions, syrups, drops, sublingual tablets, etc.

Bulc powders can be manufactured by comminuting the active substance into a finely divided form. Powders can be manufactured by comminuting the active substance into a finely-divided form and blending it with a similarly comminuted pharmaceutical carrier, e.g. an edible carbohydrate such as starch or mannitol. Where necessary, a corrigent, a preservative, a dispersant, a coloring agent, a perfume, etc. can also be added.

Capsules can be manufactured by filling said finely-divided bulc powders or powders, or granules described below for tablets, in capsule shells such as gelatin capsule shells. Preceding the filling operation, a lubricant or a fluidizing agent, such as colloidal silica, talc, magnesium stearate, calcium stearate or solid polyethylene glycol, can be blended with the powders. Improvement in the efficacy of the drug after ingestion can be expected when a disintegrator or a solubilizer, such as carboxymethylcellulose, carboxymethylcellulose calcium, low-substitution-degree hydroxypropylcellulose, croscarmellose sodium, carboxymethylstarch sodium, calcium carbonate or sodium carbonate, is added.

Soft capsules can be provided by suspending said finely divided powders in vegetable oil, polyethylene glycol, glycerin, or a surfactant and wrapping the suspension in gelatin sheets. Tablets can be manufactured by adding an excipient to said powders, granulating or slugging the mixture, adding a disintegrator and/or a lubricant, and compressing the whole composition. A powdery mixture can be prepared by mixing said finely divided powders with said diluent or a base. Where necessary, a binder (e.g. carboxymethylcellulose sodium, methylcellulose, hydroxypropylmethylcellulose, gelatin, polyvinylpyrrolidone, polyvinyl alcohol, etc.), a dissolution retardant (e.g. paraffin), a reabsorption agent (e.g. quaternary salts), and an adsorbent (e.g. bentonite, kaolin, dicalcium phosphate, etc.) can be added. The powdery mixture can be processed into granules by wetting it with a binder, e.g. a syrup, a starch paste, gum arabic, a solution of cellulose, or a solution of a high polymer, stirring to mix, drying it, and pulverizing the same. Instead of granulating such powders, it is possible to compress the powders with a tablet machine and crush the resulting slugs of crude form to prepare granules. The resulting granules can be protected against interadhesion by the addition of a lubricant such as stearic acid, a salt of stearic acid, talc or mineral oil. The mixture thus lubricated is then compressed. The resulting uncoated tablets can be coated with a film coating composition or a sugar coating composition.

The compound of the invention can be mixed with a free-flowing inert carrier and the mixture be directly compressed without resort to the above-mentioned granulation or slugging process. A transparent or translucent protective coat consisted of, for example, a hermetic shellac coat, a sugar or polymer coat, or a polishing wax coat can also be applied. Other oral compositions such as a solution, a syrup, and an elixir can also be provided in unit dosage forms each containing a predetermined amount of the drug substance. Syrups can be manufactured by dissolving the compound in suitable flavored aqueous media, while elixirs can be manufactured using nontoxic alcoholic vehicles. Suspensions can be formulated by dispersing the compound in nontoxic vehicles. Where necessary, solubilizers and emulsifiers (e.g. ethoxylated isostearyl alcohol, polyoxyethylene sorbitol ester, etc.), preservatives, and flavorants (e.g. peppermint oil, saccharin, etc.) can also be added.

Where necessary, the unit dosage formulation for oral administration can be microencapsulated. This formulation can be coated or embedded in a polymer, wax or other matrix to provide a prolonged action or sustained release dosage form.

Parenteral administration can be carried out using liquid unit dosage forms for subcutaneous, intramuscular, or intravenous injection, e.g. solutions and suspensions. Such unit dosage forms can be manufactured by suspending or dissolving a predetermined amount of the compound of the invention in an injectable nontoxic liquid vehicle, for example an aqueous vehicle or an oily vehicle, and sterilizing the resulting suspension or solution. For isotonizing an injection, a nontoxic salt or salt solution can be added. Moreover, stabilizers, preservatives, emulsifiers, etc. may also be added.

Rectal administration can be carried out by using suppositories manufactured by dissolving or suspending the compound in a low-melting water-soluble or water-insoluble solid carrier such as polyethylene glycol, caccao butter, semisynthetic oil (e.g. Witepsol®), a higher ester (e.g. myristyl palmitate) or a mixture thereof.

The toxicity of the compound of the invention is extremely low as will be described hereinafter.

BEST MODE FOR CARRYING OUT THE INVENTION

The following reference examples and examples of production of the compound of the invention and test examples using some representative species of the compound of the invention are intended to illustrate the present invention in further detail.

Reference Example 1

4-(4-Fluorophenyl)-6-hydroxy-2-methylpyrimidine (Step 1)

To 1.3 L (liters) of dry tetrahydrofuran (THF) was added 162 g of 60% sodium hydride (NaH) and 342 g of diethyl carbonate. To this mixture was added a solution of 200 g p-fluoroacetophenone in 440 ml dry THF dropwise over about 1 hour while refluxing, followed by 6 hours of refluxing. This reaction mixture was cooled, poured into iced water, neutralized with concentrated hydrochloric acid, and extracted with ethyl acetate. The organic layer was washed with water, dried over anhydrous magnesium sulfate ($MgSO_4$), and concentrated. The residue was distilled under reduced pressure to provide 291 g of ethyl 3-(4-fluorophenyl)-3-oxopropionate as pale yellow oil.

b.p. 145–150° C. (5 mmHg)

(Step 2)

A mixture of 145 g of ethyl 3-(4-fluorophenyl)-3-oxopropionate, 97.8 g of acetamidine hydrochloride, 191 g of powdered potassium carbonate, and 1.16 L of ethanol was stirred at 60–70° C. for 16 hours. This reaction mixture was filtered to remove insolubles and the filtrate was concentrated. To the residue was added water and the resultant was neutralized with acetic acid. The crystals that separated out were collected by filtration, washed with water, and dried to provide 88.7 g of the title compound as white crystals. m.p. 290–292° C. (decomp.)

In the same manner as above, the following compounds were synthesized.

4-(2-Chlorophenyl)-6-hydroxy-2-methylpyrimidine 4-(2 4-Dichlorophenyl)-6-hydroxy-2-methylpyrimidine
 m.p. 271–274° C.

2.5-Dimethyl-4-(4-fluorophenyl)-6-hydroxypyrimidine
 m.p. 242–243° C.

4-(4-Fluorophenyl)-6-hydroxy-5-methylpyrimidine
 m.p. 228–229° C.

Reference Example 2

4-Chloro-6-(4-fluorophenyl)-2-methylpyrimidine

To 21 g of 4-(4-fluorophenyl)-6-hydroxy-2-methylpyrimidine was added 63 ml of phosphorus oxychloride and the mixture was refluxed for 1 hour. This reaction mixture was cooled, poured into iced water, and neutralized with 28% aqueous ammonia and the crystals that separated out were collected by filtration. The crystals were washed with water and dried to provide 21 g of the title compound.
 m.p. 95–98° C.

In the same manner as above, the following compounds were synthesized.

4-Chloro-6-(2-chlorophenyl)-2-methylpyrimidine
 m.p. 88–90° C.

4-Chloro-6-(2,4-dichlorophenyl)-2-methylpyrimidine
 m.p. 104–105° C.

4-Chloro-2,5-dimethyl-6-(4-fluorophenyl)pyrimidine
 m.p. 110–113° C.

4-Chloro-6-(2-fluorophenyl)-5-methylpyrimidine
 m.p. 88–90° C.

Reference Example 3

4-(4-Chlorobutoxy)-2-(4-fluorophenyl)-6-methylpyridine hydrochloride

A mixture of 2.5 g of 2-(4-fluorophenyl)-4-hydroxy-6-methylpyridine, 3.16 g of 1-bromo-4-chlorobutane, 1.7 g of silver carbonate, and 100 ml of toluene was refluxed for 40 hours. This reaction mixture was filtered to remove insolubles and the filtrate was concentrated. The residue was purified with silica gel column chromatography to provide 1.45 g of the title compound as white crystals.
 m.p. 59–61° C.

Reference Example 4

4-(4-Fluorophenyl)-2-hydroxy-6-methylpyridine

A mixture of 5 g of 4-fluorobenzoylacetone, 1.66 g of urea, 25 ml of ethanol, and 3.8 ml of concentrated hydrochloric acid was refluxed for 20 hours. This reaction mixture was cooled, poured into iced water, made basic with aqueous solution of potassium carbonate, and neutralized with acetic acid. The crystals that separated out were collected by filtration, washed with isopropyl ether, and dried to provide 2.65 g of pale yellow crystals.
 m.p. 265–268° C.

Reference Example 5

4,6-Bis(4-fluorophenoxy)-2-methylpyrimidine

In a solvent mixture of 13 ml THF and 2.7 ml DMF was dissolved 448 mg of 4-fluorophenol and while the solution was stirred at room temperature, 160 mg of 60% NaH was added in small portions. The mixture was further stirred at the same temperature for 30 minutes. Then, 326 mg of 4,6-dichloro-2-methylpyrimidine was added and the mixture was further stirred at room temperature for 12 hours. This reaction mixture was poured into iced water and extracted with ethyl acetate. The organic layer was washed with water, dried over $MgSO_4$, and concentrated under reduced pressure. The residue, 700 mg, was purified with silica gel column chromatography (Wakogel™ C-200, n-hexane-ethyl acetate=9:1) and recrystallized from n-hexane to provide 461 mg of white crystals.
 m.p. 93–97° C.

In the same manner as above, the following compound was synthesized.

4,6-Bis(4-fluorophenylthio)-2-methylpyrimidine
m.p. 134–136° C.

Reference Example 6
4-(4,5-Epoxypentyloxy)-6-(4-fluorophenyl)-2-methylpyrimidine (Step 1)

A mixture of 2 g of 4-(4-fluorophenyl)-6-hydroxy-2-methylpyrimidine obtained in Reference Example 1, 2.8 g of 5-bromo-1-pentene, 1.5 g of silver carbonate, and 80 ml of toluene was refluxed for 22 hours. This reaction mixture was filtered to remove insolubles and the filtrate was concentrated. The residue was purified with silica gel column chromatography to provide 370 mg of 4-(4-fluorophenyl)-2-methyl-6-(4-pentenyl)pyrimidine as white crystals.

m.p. 44.5–45.5° C.

(Step 2)

In 5 ml of methylene chloride was dissolved 350 mg of 4-(4-fluorophenyl)-2-methyl-6-(4-pentenyl)pyrimidine. To this solution on an ice-water bath was added 217 mg of 70% m-chloroperbenzoic acid with stirring. This mixture was then stirred at room temperature for 18 hours. The reaction mixture thus obtained was concentrated and n-hexane and ethyl acetate were added to the residue. The mixture was washed with aqueous solution of sodium hydrogen carbonate four times and further with water, dried over MgSO$_4$, and concentrated. The residue was purified with silica gel column chromatography to provide 160 mg of the title compound as white crystals.

m.p. 63.0–64.0° C.

Reference Example 7
2-Chloro-4-methyl-6-phenyl-1,3,5-triazine (Step 1)

To 50 g of 2,4,6-trichloro-1,3,5-triazine was added 300 ml of dry tetrahydrofuran and while the mixture was stirred at room temperature, 150 ml of 2M phenylmagnesium bromide-tetrahydrofuran was added dropwise over about 30 minutes. After completion of dropwise addition, the mixture was stirred at room temperature for 1 hour, and then concentrated. To the residue was added iced water and the resultant was extracted with ether. The extract was washed with water, dried over MgSO$_4$, and concentrated. The resulting crystal crop was recrystallized from isopropyl alcohol to provide 21.1 g of 2,4-dichloro-6-phenyl-1,3,5-triazine as pale yellow crystals.

(Step 2)

In 85 ml of dry tetrahydrofuran was dissolved 17 g of 2,4-dichloro-6-phenyl-1,3,5-triazine. To this solution on an ice-water bath was added 135 ml of 1M methylmagnesium bromide-tetrahydrofuran dropwise over about 30 minutes. After completion of dropwise addition, the mixture was stirred at room temperature for 2 hours. This reaction mixture was poured into iced water and extracted with ethyl acetate. The extract was washed with water, dried over MgSO$_4$, and concentrated. The residue was purified with silica gel column chromatography to provide 3.6 g of the title compound as white crystals.

Reference Example 8
2-Benzyloxyphenyl-4-hydroxy-6-methylpyrimidine (Step 1)

In 200 ml of methanol was suspended 23 g of 4-benzyloxybenzonitrile and hydrogen chloride gas was bubbled through the suspension on an ice-water bath for about 1 hour. Thereafter, the mixture was stirred at the same temperature for 2 hours and, then, at room temperature for 1.5 hours. To this reaction mixture was added ether and the crystals that separated out were collected by filtration to provide 28 g of white crystals. These crystals were suspended in 200 ml of methanol and, on an ice-water bath, ammonia gas was bubbled through the suspension for about 1 hour. The mixture was then stirred at room temperature for 15 hours. This reaction mixture was concentrated and ethyl acetate was added to the residue. The crystals that separated out were collected by filtration and dried to provide 21.6 g of 4-benzyloxybenzamidine hydrochloride as white crystals.

(Step 2)

A mixture of 12 g of 4-benzyloxybenzamidine hydrochloride, 6.3 g of ethyl acetoacetate, 13.9 g of potassium carbonate, and 144 ml of ethanol was refluxed for 24 hours. This reaction mixture was filtered to remove insolubles and the filtrate was concentrated. To the residue was added water and the resultant was neutralized with acetic acid. The crystals that separated out were collected by filtration, rinsed with water, and dried to provide 12.0 g of the title compound as white crystals.

EXAMPLE 1
4-(4-Fluorophenyl)-2-methyl-6-(5-piperidinopentyloxy)pyrimidine hydrochloride To a solvent mixture of 155 ml dry THF and 33 ml dry DMF was added 3.59 g of 60% sodium hydride (NaH) and while the mixture was stirred at room temperature, 7.06 g of 5-piperidino-1-pentanol was added. The mixture was further stirred for 10 minutes. Then, 10 g of 4-chloro-6-(4-fluorophenyl)-2-methylpyrimidine was added and the mixture was stirred at room temperature for 20 hours. This reaction mixture was poured into iced water and extracted with ethyl acetate. The organic layer was washed with water, dried over MgSO$_4$, and concentrated. The residue was purified with silica gel column chromatography (Wakogel™ C-200, chloroform containing 1% of methanol) to give a pale yellow oil. This oil was dissolved in methanol and the solution was adjusted to pH 5 with 1N-HCl, and concentrated. To the residue was added ether and the crystals that separated out were collected by filtration. This crystal crop was recrystallized from acetonitrile to provide white crystals of type I or II.

Crystals of type I m.p. 184–186° C.

Elemental analysis for $C_{21}H_{28}FN_3O \cdot HCl$ Calcd. (%): C, 64.03; H, 7.42; N, .10.67 Found (%): C, 63.82; H, 7.39; N, 10.70.

Crystals of type II m.p. 182–184° C.

Elemental analysis for $C_{21}H_{28}FN_3O \cdot HCl$ Calcd. (%): C, 64.03; H, 7.42; N, 10.67 Found (%): C., 63.80; H, 7.38; N, 10.74.

In the same manner as Example 1, the following compounds were synthesized.

EXAMPLE 2
4-(4-Fluorophenyl)-2-methyl-6-(4-piperidinobutoxy)pyrimidine hydrochloride m.p. 174–176° C.

EXAMPLE 3
4-(4-Fluorophenyl)-2-methyl-6-(6-piperidinohexyloxy) primidine hydrochloride
m.p. 190.5–192° C.
Elemental analysis for $C_{22}H_{30}FN_3O\cdot HCl$ Calcd. (%): C, 64.77; H, 7.66; N, 10.30 Found (%): C, 64.49; H, 7.66; N, 10.48.

EXAMPLE 4
2-(4-Fluorophenyl)-4-methyl-6-(4-piperidinobutoxy) pyrimidine hydrochloride
m.p. 168–172° C.
Elemental analysis for $C_{20}H_{26}FN_3O\cdot HCl$ Calcd. (%): C, 63.23; H, 6.90; N, 11.06 Found (%): C, 63.10; H, 7.11; N, 10.80.

EXAMPLE 5
2-(4-Fluorophenyl)-4-methyl-6-(5-piperidinopentyloxy) pyrimidine hydrochloride
m.p. 184–185° C.
Elemental analysis for $C_{21}H_{28}FN_3O\cdot HCl$ Calcd. (%): C, 64.03; H, 7.42; N, 10.67 Found (%): C, 63.80; H, 7.52; N, 10.60.

EXAMPLE 6
4-(2-Chlorophenyl)-2-methyl-6-(4-piperidinobutoxy) pyrimidine hydrochloride
m.p. 147–149° C.
Elemental analysis for $C_{20}H_{26}ClN_3O\cdot HCl$ Calcd. (%): C, 60.01; H, 6.87; N, 10.60 Found (%): C, 60.43; H, 7.05; N, 10.80.

EXAMPLE 7
S 4-(2,4-Dichlorophenyl)-2-methyl-6-(4-piperidinobutoxy)pyrimidine hydrochloride
m.p. 144–146° C.
Elemental analysis for $C_{20}H_{25}Cl_2N_3O\cdot HCl$ Calcd. (%): C, 55.76; H, 6.08; N, 9.75 Found (%): C, 55.40; H, 6.21; N, 9.74.

EXAMPLE 8
4-(4-Fluorophenyl)-2-methyl-6-[4-(4-phenylpiperidino) butoxy]pyrimidine hydrochloride
m.p. 169–171° C.
Elemental analysis for $C_{26}H_{30}FN_3O\cdot HCl$ Calcd. (%): C, 68.48; H, 6.85; N, 9.21 Found (%): C, 68.20; H, 7.01; N, 9.27.

EXAMPLE 9
2-(4-Fluorophenyl)-4-methyl-6-[4-(4-phenylpiperidino) butoxy]pyrimidine hydrochloride
m.p. 148–153° C.
Elemental analysis for $C_{26}H_{30}FN_3O\cdot HCl$ Calcd. (%): C, 68.48; H, 6.85; N, 9.21 Found (%): C, 68.20; H, 6.89; N, 9.03.

EXAMPLE 10
2-(4-Fluorophenyl)-4-methyl-6-[4-(4-phenylpiperazino) butoxy]pyrimidine maleate
After the same reaction procedure as described in Example 1, the title compound was obtained by using a solution of maleic acid in ethanol.
m.p. 218° C. (decomp.)
Elemental analysis for $C_{25}H_{29}FN_4O\cdot C_4H_4O_4$ Calcd. (%): C, 64.91; H, 6.20; N, 10.44 Found (%): C, 64.93; H, 6.24; N, 10.32.

In the same manner as Example 1 or Example 11, the following compounds were synthesized.

EXAMPLE 11
2-(4-Fluorophenyl)-4-methyl-6-[4-( 4-phenylpiperazino) butoxy]pyrimidine maleate
m.p. 155–156° C.
Elemental analysis for $C_{25}H_{29}FN_4O\cdot C_4H_4O_4$ Calcd. (%): C, 64.91; H, 6.20; N, 10.44 Found (%): C, 64.81; H, 6.29; N, 10.48.

EXAMPLE 12
2.4-Bis(4-fluorophenyl)-6-(4-piperidinobutoxy)pyrimidine hydrochloride
m.p. 207–208.5° C.
Elemental analysis for $C_{25}H_{27}F_2N_3O\cdot HCl$ Calcd. (%): C, 65.28; H, 6.14; N, 9.14 Found (%): C, 65.05; H, 6.26; N, 9.08.

EXAMPLE 13
2,4-Bis(4-fluorophenyl)-6-(5-piperidinopentyloxy) pyrimidine hydrochloride
m.p. 196–198.50° C.
Elemental analysis for $C_{26}H_{29}F_2N_3O\cdot HCl$ Calcd. (%): C, 65.88; H, 6.38; N, 8.87 Found (%): C, 65.50; H, 6.44; N, 8.64.

EXAMPLE 14
4-(4-Hydroxyphenyl)-2-methyl-6-[4-(4-phenylpiperidino) butoxy]pyrimidine hydrochloride
Using 4-(4-phenylpiperidino)-1-butanol and 6-(4-benzyloxyphenyl)-4-chloro-2-methylpyrimidine, the procedure of Reference Example 25, which appears hereinafter, was otherwise followed to provide the title compound.
m.p. 182–183° C.
Elemental analysis for $C_{26}H_{31}N_3O_2\cdot HCl$ Calcd. (%): C, 68.78; H, 7.10; N, 9.26 Found (%): C, 68.58; H, 6.96; N, 8.99.

EXAMPLE 15
2-(4-Fluorophenyl)-4-(4-piperidinobutoxy)-6-methylpyridine hydrochloride
A mixture of 1.45 g of the 4-(4-chlorobutoxy)-2-(4-fluorophenyl)-6-methylpyridine obtained in Reference Example 3, 1.26 g of piperidine, and 12 ml of DMF was stirred at 100° C. for 1.5 hours. This reaction mixture was cooled, poured into iced water, and extracted with ethyl acetate. The organic layer was washed with an aqueous solution of sodium chloride several times, dried over MgSO$_4$, and then concentrated. The residue was purified with silica gel column chromatography to provide 1.2 g of the objective compound as oil. This oil was dissolved in methanol and the solution was adjusted to pH 5 with 3.5 ml of 1N-HCl and concentrated. To the residue was added ether and the resulting crystal crop was collected by filtration and recrystallized from the mixture of acetonitrile and ether to provide 1.02 g of the title compound as white crystals.
m.p. 164–166° C.
Elemental analysis for $C_{21}H_{27}FN_2O\cdot HCl$ Calcd. (%): C, 66.57; H, 7.45; N, 7.39 Found (%): C, 66.21; H, 7.45; N, 7.09.

Elemental analysis for $C_{20}H_{26}FN_3O\cdot HCl$ Calcd. (%): C, 63.23; H, 7.16; N, 11.06 Found (%): C, 62.83; H, 7.23; N, 11.01.

In the same manner as Example 15, the following compounds were synthesized.

EXAMPLE 16
4-(4-Fluorophenyl)-2-methyl-6-(3-piperidinopropoxy) pyridine hydrochloride
m.p. 135° C.
Elemental analysis for $C_{20}H_{25}FN_2O \cdot HCl$ Calcd. (%): C, 65.83; H, 7.18; N, 7.68 Found (%): C, 65.40; H, 7.24; N, 7.44.

EXAMPLE 17
4-(4-Fluorophenyl)-2-methyl-6-(4-piperidinobutoxy) pyridine hydrochloride
m.p. 148.5–150.5° C.
Elemental analysis for $C_{21}H_{27}FN_2O \cdot HCl$ Calcd. (%): C, 66.57; H. 7.45; N, 7.39 Found (%): C, 66.54; H, 7.57; N, 7.41.

EXAMPLE 18
4-(4-Fluorophenyl)-2-methyl-6-(5-piperidinopentyloxy) pyridine hydrochloride
m.p. 138–140° C.
Elemental analysis for $C_{22}H_{29}FN_2O \cdot HCl$ Calcd. (%): C, 67.25; H, 7.70; N, 7.13 Found (%): C, 67.00; H, 7.68; N, 6.95.

EXAMPLE 19
2,4-Bis(4-fluorophenyl)-6-(4-piperidinobutoxy)pyridine hydrochloride
m.p. 219–220.5° C.
Elemental analysis for $C_{26}H_{28}F_2N_2O \cdot HCl$ Calcd. (%): C, 68.04; H, 6.37; N, 6.10 Found (%): C, 68.40; H, 6.37; N, 6.20.

EXAMPLE 20
2.4-Bis(4-fluorophenyl)-6-(5-piperidinopentyloxy)pyridine hydrochloride
m.p. 165–166.5° C.
Elemental analysis for $C_{27}H_{30}F_2N_2O \cdot HCl$ Calcd. (%): C, 68.56; H, 6.61; N, 5.92 Found (%): C, 68.57; H. 6.74; N, 5.99.

In the same manner as Example 1, the following compound was synthesized.

EXAMPLE 21
4-(4-Fluorophenyl)-2-methyl-6-(1-methyl-4-piperidinobutoxy)pyrimidine hydrochloride
m.p. 146° C.
Elemental analysis for $C_{21}H_{28}FN_3O \cdot HCl$ Calcd. (%): C, 64.03; H, 7.42; N, 10.67 Found (%): C, 63.90; H, 7.44; N, 10.42.

EXAMPLE 22
4-(4-Fluorophenyl)-6-[5-(4-hydroxypiperidino)pentyloxy]-2-methylpyrimidine hydrochloride
A mixture of 4 g of the 4-(4-fluorophenyl)-6-hydroxy-2-methylpyrimidine obtained in Reference Example 1, 13.5 g of 1,5-dibromopentane, 2.97 g of silver carbonate, and 160 ml of toluene was refluxed for 50 hours. This reaction mixture was filtered to remove insolubles and the filtrate was concentrated. The residue was purified with silica gel column chromatography to provide 2.6 g of colorless oil. To 800 mg of this oil was added 275 mg of 4-hydroxypiperidine as well as 468 mg of potassium carbonate and 8 ml of acetonitrile and the mixture was stirred at room temperature for 19 hours. This reaction mixture was poured into iced water and extracted with ethyl acetate. The extract was washed with aqueous solution of sodium chloride, dried over $MgSO_4$, and concentrated. The residue was purified with silica gel column chromatography to provide 600 mg of oil. This oil was dissolved in methanol and the solution was adjusted to pH 5 with 1.61 ml of 1N-HCl, and concentrated. To the residue was added isopropyl ether and the crystals that separated out were collected by filtration and recrystallized from acetonitrile-isopropyl ether to provide 559 mg of the title compound as white crystals.
m.p. 167.0–169.5° C.
Elemental analysis for $C_{21}H_{28}FN_3O_2 \cdot HCl$ Calcd. (%): C, 61.53; H, 7.13; N, 10.25 Found (%): C, 61.42; H, 7.09; N, 10.47.

EXAMPLE 23
4-(4-Fluorophenyl)-6-(4-hydroxy-5-piperidinopentyloxy)-2-methylpyrimidine hydrochloride
A mixture of 160 mg of the 4-(4,5-epoxypentyloxy)-6-(4-fluorophenyl)-2-methylpyrimidine obtained in Reference Example 6, 140 mg of piperidine, and 3 ml of acetonitrile was stirred at 80° C. for 20 hours. This reaction mixture was cooled and then poured into iced water and extracted with ethyl acetate. The extract was washed with aqueous solution of sodium chloride, dried over $MgSO_4$, and concentrated. The residue was purified with silica gel column chromatography to provide 158 mg of oil. This oil was dissolved in methanol and the solution was adjusted to pH 5 with 0.42 ml of 1N-HCl and concentrated. To the residue was added isopropyl ether and the resulting crystal crop was collected by filtration and recrystallized from acetonitrile to provide 121 mg of the title compound as white crystals.
m.p. 149.0–150.5° C.
Elemental analysis for $C_{21}H_{28}FN_3O_2 \cdot HCl$ Calcd. (%): C, 61.53; H, 7.13; N, 10.25 Found (%): C, 61.36; H, 7.06; N, 10.25.

In the same manner as Example 1, the following compounds were synthesized.

EXAMPLE 24
4-[5-(N,N-diethylamino)pentyloxy]-6-(4-fluorophenyl)-2-methylpyrimidine hydrochloride
m.p. 134.5–136.5° C.
Elemental analysis for $C_{20}H_{28}FN_3O \cdot HCl \cdot 1/4H_2O$ Calcd. (%): C, 62.17; H, 7.69; N, 10.87 Found (%): C, 62.15; H, 7.68; N, 10.84.

EXAMPLE 25
2-Methyl-4-(5-piperidinopentyloxy)-6-(2-thienyl) pyrimidine hydrochloride
m.p. 192.5–194.0° C.
Elemental analysis for $C_{19}H_{27}N_3OS \cdot HCl$ Calcd. (%): C, 59.75; H, 7.39; N, 11.00 Found (%): C, 59.35; H, 7.32; N, 10.98.

EXAMPLE 26
2-Methyl-4-(5-piperidinopentyloxy)-6-(pyridin-4-yl) pyrimidine hydrochloride
m.p. 178.5–179.5° C.
Elemental analysis for $C_{20}H_{28}N_4O \cdot HCl$ Calcd. (%): C, 63.73; H, 7.75; N, 14.86 Found (%): C, 63.38; H, 7.70; N, 14.86.

EXAMPLE 27
4-(4-Fluorophenyl)-6-methyl-2-(5-piperidinopentyloxy) pyrimidine hydrochloride Using 4-(4-fluorophenyl)-2-hydroxy-6-methylpyrimidine obtained in Reference Example 4, the procedure of Example 22 was otherwise carried out to provide the title compound.

m.p. 173.5–175.0° C.

Elemental analysis for $C_{21}H_{28}FN_3O.HCl$ Calcd. (%): C, 64.03; H, 7.42; N, 10.67 Found (%): C, 63.85; H, 7.48; N, 10.82.

In the same manner as Example 27, the following compounds were synthesized.

EXAMPLE 28
4-(4-Fluorophenyl)-6-methyl-2-(5-piperidinopentylthio) pyrimidine hydrochloride m.p. 156–158° C.

Elemental analysis for $C_{21}H_{28}FN_3S.HCl.1/4H_2O$ Calcd. (%): C, 60.85; H, 7.17; N, 10.14 Found (%): C, 60.80; H, 7.05; N, 10.02.

In the same manner as Example 1, the following compound was synthesized.

EXAMPLE 29
4-(4-Fluorophenyl)-2-methyl-6-(3-piperidinopropylthio) pyrimidine hydrochloride m.p. 192–194° C.

Elemental analysis for $C_{19}H_{24}FN_3S.HCl.1/4H_2O$ Calcd. (%): C, 59.05; H, 6.59; N, 10.87 Found (%): C, 58.96; H, 6.54; N, 10.79.

EXAMPLE 30
4-(4-Fluorophenoxy)-2-methyl-6-(5-piperidinopentyloxy) pyrimidine hydrochloride In a solvent mixture of 4.3 ml THF and 0.9 ml DMF was suspended 51 mg of 60% NaH. While this suspension was stirred at room temperature, 218 mg of 5-piperidino-1-pentanol was added and the mixture was stirred at room temperature for 30 minutes. Then, 400 mg of the 2,4-bis(4-fluorophenoxy)-6-methylpyrimidine obtained in Reference Example 5 was added thereto and the mixture was stirred at room temperature for 18 hours. This reaction mixture was poured into iced water and extracted with ethyl acetate. The organic layer was washed with water, dried over MgSO$_4$, and concentrated under reduced pressure. As a result, 600 mg of an oily residue was obtained. This oil was purified with silica gel column chromatography [Wakogel™ C-200, chloroform→chloroform-methanol (25:1)] to provide 200 mg of light-yellow oil. A 190 mg of this oil was dissolved in methanol and the solution was adjusted to pH 5 with 0.5 ml of 1N-HCl and concentrated under reduced pressure. To the residue was added ether and the resulting crystals were collected by filtration. This crystal crop was washed with ether and recrystallized from acetone to provide 137 mg of the title compound as white crystals.

m.p. 164–165° C.

Elemental analysis for $C_{21}H_{28}FN_3O_2.HCl$ Calcd. (%): C, 61.53; H, 7.13; N, 10.25 Found (%): C, 61.40; H, 7.08; N, 10.26.

EXAMPLE 31
4-(4-Fluorophenylthio)-2-methyl-6-(5-piperidinopentyloxy) pyrimidine hydrochloride Using the 4,6-bis(4-fluorophenylthio)-2-methyl-pyrimidine obtained in the same manner as in Reference Example 5, the procedure was otherwise carried out in the same manner as Exampel 30 to provide the title compound as light-yellow crystals.

m.p. 127–131° C. (as recrystallized from acetone/ether)

Elemental analysis for $C_{21}H_{28}FN_3OS.HCl.1/2H_2O$ Calcd. (%): C, 57.98; H, 6.72; N, 9.66 Found (%): C, 58.03; H, 6.86; N, 9.62.

In the same manner as Example 1, the following compounds were synthesized.

EXAMPLE 32
4-(4-Fluorobenzyl)-2-methyl-6-(5-piperidinopentyloxy) pyrimidine hydrochloride m.p. 109–115° C.

Elemental analysis for $C_{22}H_{30}FN_3O.HCl.H_2O$ Calcd. (%): C, 62.03; H, 7.81; N, 9.86 Found (%): C, 62.30; H, 8.10; N, 9.94.

EXAMPLE 33
2-Methyl-4-phenethyl-6-(5-piperidinopentyloxy)pyrimidine hydrochloride m.p. 128–130° C.

Elemental analysis for $C_{23}H_{33}N_3O.HCl.1/2H_2O$ Calcd. (%): C, 66.89; H, 8.54; N, 10.17 Found (%): C, 66.83; H, 8.35; N, 10.17.

EXAMPLE 34
2,5-Dimethyl-4-(4-fluorophenyl)-6-(4-piperidinobutoxy) pyrimidine hydrochloride m.p. 154–157° C.

Elemental analysis for $C_{21}H_{28}FN_3O.HCl$ Calcd. (%): C, 64.03; H, 7.42; N, 10.67 Found (%): C, 63.86; H, 7.30; N, 10.61.

EXAMPLE 35
4-(4-Fluorophenyl)-5-methyl-6-(4-piperidinobutoxy) pyrimidine hydrochloride m.p. 146–149° C.

Elemental analysis for $C_{20}H_{26}FN_3O.HCl$ Calcd. (%): C, 63.23; H, 7.16; N, 11.06 Found (%): C, 63.01; H, 7.10; N, 11.08.

EXAMPLE 36
2-Methyl-4-phenyl-6-(4-piperidinobutoxy)-1,3,5-triazine hydrochloride m.p. 177–178° C.

Elemental analysis for $C_{19}H_{26}N_4O.HCl$ Calcd. (%): C, 62.88; H, 7.50; N, 15.44 Found (%): C, 62.55; H, 7.68; N, 15.28.

EXAMPLE 37
2-Methyl-4-phenyl-6-(3-piperidinopropoxy)-1.3,5 -triazine hydrochloride m.p. 175–178° C.

Elemental analysis for $C_{18}H_{24}N_4O.HCl$ Calcd. (%): C, 61.97; H, 7.22; N, 16.06 Found (%): C, 61.87; H, 7.41; N, 16.14.

EXAMPLE 38
2-(4-Chlorophenyl)-4-methyl-6-(3-piperidinopropoxy)-1,3,5-triazine maleate m.p. 125–128° C.

Elemental analysis for $C_{18}H_{23}ClN_4O.C_4H_4O_4.1/4H_2O$ Calcd. (%): C, 56.53; H, 5.93; N, 11.99 Found (%): C, 56.22; H, 6.07; N, 12.01.

EXAMPLE 39
2-Methyl-4-phenyl-6-[3-(4-phenylpiperidino)propoxy]-1,3,5-triazine hydrochloride
m.p. 159–163° C.
Elemental analysis for $C_{24}H_{28}N_4O \cdot HCl \cdot 1/2H_2O$ Calcd. (%): C, 66.58; H, 6.75; N, 12.94 Found (%): C, 66.56; H, 7.15; N, 13.30.

EXAMPLE 40
2-Methyl-4-(2-naphthyl)-6-(4-piperidinobutoxy)pyrimidine hydrochloride
m.p. 174–175° C.
Elemental analysis for $C_{24}H_{29}N_3O \cdot HCl$ Calcd. (%): C, 69.97; H, 7.34; N, 10.20 Found (%): C, 69.80; H, 7.20; N, 10.21.

Production examples for the compound of formula [I] are presented below. Where the procedures are not particularly described, the procedure of Example 1 was followed.

Reference Example 9
4-(4-Fluorophenyl)-2-methyl-6-(2-piperidinoethoxy)pyrimidine hydrochloride
m.p. 198–199° C.
Elemental analysis for $C_{18}H_{22}FN_3O \cdot HCl$ Calcd. (%): C, 61.45; H, 6.59; N, 11.94 Found (%): C, 61.23; H, 6.78; N, 11.74.

Reference Example 10
4-(4-Fluorophenyl)-2-methyl-6-(3-piperidinopropoxy)pyrimidine hydrochloride
m.p. 195.5–197° C.
Elemental analysis for $C_{19}H_{24}FN_3O \cdot HCl$ Calcd. (%): C, 62.37; H, 6.89; N, 11.48 Found (%): C, 62.00; H, 7.03; N, 11.13.

Reference Example 11
2-(4-Fluorophenyl)-4-methyl-6-(2-piperidinoethoxy)pyrimidine hydrochloride
m.p. 216–218° C.
Elemental analysis for $C_{18}H_{22}FN_3O \cdot HCl$ Calcd. (%): C, 61.45; H, 6.56; N, 11.94 Found (%): C, 61.10; H, 6.78; N, 11.63.

Reference Example 12
2-(4-Fluorophenyl)-4-methyl-6-(3-piperidinopropoxy)pyrimidine hydrochloride
m.p. 205–206.5° C.
Elemental analysis for $C_{19}H_{24}FN_3O \cdot HCl$ Calcd. (%): C, 62.37; H, 6.89; N, 11.48 Found (%): C, 62.01; H, 6.99; N, 11.47.

Reference Example 13
2-(4-Chlorophenyl)-4-methyl-6-(3-piperidinopropoxy)pyrimidine hydrochloride
m.p. 212–214° C.
Elemental analysis for $C_{19}H_{24}ClN_3O \cdot HCl$ Calcd. (%): C, 59.69; H, 6.59; N, 10.99 Found (%): C, 59.23; H, 6.53; N, 10.80.

Reference Example 14
4-(4-Fluorophenyl)-2-methyl-6-[2-(4-phenylpiperidino)ethoxy]pyrimidine hydrochloride
m.p. 184–186° C.
Elemental analysis for $C_{24}H_{26}FN_3O \cdot HCl$ Calcd. (%): C, 67.36; H, 6.36; N, 9.82 Found (%): C, 67.10; H, 6.73; N, 9.78.

Reference Example 15
4-(4-Fluorophenyl)-2-methyl-6-[3-(4-phenylpiperidino)propoxy]pyrimidine hydrochloride
m.p. 169–171° C.
Elemental analysis for $C_{25}H_{28}FN_3O \cdot HCl$ Calcd. (%): C, 68.09; H, 6.40; N, 9.53 Found (%): C, 67.80; H, 6.60; N, 9.31.

Reference Example 16
2-(4-Fluorophenyl)-4-methyl-6-[2-(4-phenylpiperidino)ethoxy]pyrimidine hydrochloride
m.p. 211–212° C.
Elemental analysis for $C_{24}H_{26}FN_3O \cdot HCl$ Calcd. (%): C, 67.36; H, 6.36; N, 9.82 Found (%): C, 67.01; H, 6.49; N, 9.61.

Reference Example 17
2-(4-Fluorophenyl)-4-methyl-6-[3-(4-phenylpiperidino)propoxy]pyrimidine hydrochloride
m.p. 195–198° C.
Elemental analysis for $C_{25}H_{28}FN_3O \cdot HCl$ Calcd. (%): C, 67.94; H, 6.61; N, 9.51 Found (%): C, 67.82; H, 6.50; N, 9.49.

Reference Example 18
2-(4-Chlorophenyl)-4-methyl-6-[2-(4-phenylpiperidino)ethoxy)pyrimidine hydrochloride
m.p. 208.5–210° C.
Elemental analysis for $C_{24}H_{26}ClN_3O \cdot HCl$ Calcd. (%): C, 64.86; H, 6.12; N, 9.46 Found (%): C, 64.62; H, 6.10; N, 9.42

Reference Example 19
2-(4-Fluorophenyl)-4-[3-[4-(4-fluorophenyl)-1,2,3,6-tetrahydropyridin-1-yl]propoxy]-6-methylpyrimidine. hydrochloride
m.p. 197.5–199.5° C.
Elemental analysis for $C_{25}H_{25}F_2N_3O \cdot HCl$ Calcd. (%): C, 65.57; H, 5.72; N, 9.18 Found (%): C, 65.30; H, 5.68; N, 9.12.

Reference Example 20
2-(4-Fluorophenyl)-4-methyl-6-[3-(4-phenyl-1,2,3,6-tetrahydropyridin-1-yl)propoxy]pyrimidine hydrochloride
m.p. 197–199° C.
Elemental analysis for $C_{25}H_{26}FN_3O \cdot HCl$ Calcd. (%): C, 68.25; H, 6.19; N, 9.55 Found (%): C, 68.08; H, 6.24; N, 9.31.

Reference Example 21
2-(4-Fluorophenyl)-4-[3-[4-(4-fluorophenyl)piperidino]propoxy]-6-methylpyrimidine hydrochloride
m.p. 186–187° C.
Elemental analysis for $C_{25}H_{27}F_2N_3O \cdot HCl$ Calcd. (%): C, 65.28; H, 6.14; N, 9.14 Found (%): C, 64.90; H, 6.23; N, 8.90.

Reference Example 22
2-(4-Fluorophenyl)-4-methyl-6-[3-[4-(pyridin-4-yl)piperidino]propoxy]pyrimidine hydrochloride
m.p. 186–187° C.
Elemental analysis for $C_{24}H_{27}FN_4O \cdot HCl$ Calcd. (%): C, 65.08; H, 6.37; N, 12.65 Found (%): C, 64.80; H, 6.46; N, 12.35.

Reference Example 23
4-(4-Fluorophenyl)-2-methyl-6-[3-(4-phenylpiperazino)propoxy]pyrimidine maleate m.p. 158–159° C.

Elemental analysis for $C_{24}H_{27}FN_4O \cdot C_4H_4O_4$ Calcd. (%): C, 64.36; H, 5.98; N, 10.72 Found (%): C, 64.02; H, 5.93; N, 10.60.

Reference Example 24

2-(4-Fluorophenyl)-4-methyl-6-[3-(4-phenylpiperazino) propoxy]pyrimidine maleate m.p. 174–175° C.

Elemental analysis for $C_{24}H_{27}FN_4O \cdot C_4H_4O_4$ Calcd. (%): C, 64.36; H. 5.98; N, 10.72 Found (%): C, 64.62; H, 6.01; N, 10.79.

Reference Example 25

2-(4-Hydroxyphenyl)-4-methyl-6-(3-piperidinopropoxy) pyrimidine hydrochloride

To a solvent mixture of 13 ml dry THF and 1.5 ml dry DMF was added 258 mg of 60% sodium hydride (NaH). While this mixture was stirred at room temperature, 461 mg of 3-piperidino-1-propanol was added thereto, followed by 10 minutes' stirring. To this reaction mixture was added 1 g of the 2-(4-benzyloxyphenyl)-4-chloro-6-methylpyrimidine obtained in Reference Example 8 and the mixture was stirred at room temperature for 48 hours. This reaction mixture was poured into iced water and extracted with ethyl acetate. The organic layer was washed with water, dried over $MgSO_4$, and concentrated. The residue was purified with silica gel column chromatography (Wakogel™ C-200; chloroform) to provide 1.08 g of pale yellow oil. This oil was dissolved in methanol and subjected to catalytic reduction in the presence of 5% palladium-on-carbon (Pd/C) at atmospheric temperature and pressure. The resulting reaction mixture was filtered and the filtrate was concentrated. The residue was dissolved in methanol and the solution was adjusted to pH 5 with 1N-HCl and concentrated. To the residue was added ether and the crystals that formed were collected. This crystal crop was recrystallized from methanol to provide 572 mg of the title compound as white crystals.

m.p. 248–249° C.

Elemental analysis for $C_{19}H_{25}N_3O_2 \cdot HCl$ Calcd. (%): C, 62.71; H, 7.20; N, 11.55 Found (%): C, 62.36; H, 7.22; N, 11.76.

The following compounds were synthesized in the same manner.

Reference Example 26

4-(4-Hydroxyphenyl)-2-methyl-6-(2-piperidinoethoxy) pyrimidine hydrochloride m.p. 301° C.

Elemental analysis for $C_{18}H_{23}N_3O_2 \cdot HCl$ Calcd. (%): C, 61.80; H, 6.91; N, 12.01 Found (%): C, 61.50; H, 6.83; N, 11.87.

Reference Example 27

4-(4-Hydroxyphenyl)-2-methyl-6-(3-piperidinopropoxy) pyrimidine hydrochloride m.p. 234–235° C.

Elemental analysis for $C_{19}H_{25}N_3O_2 \cdot HCl$ Calcd. (%): C, 62.71; H, 7.20; N, 11.55 Found (%): C, 62.45; H, 7.24; N, 11.51.

Reference Example 28

4-(4-Hydroxyphenyl)-2-methyl-6-[2-(4 -phenylpiperidino) ethoxy]pyrimidine hydrochloride m.p. 185° C. (decomp.)

Elemental analysis for $C_{24}H_{27}N_3O_2 \cdot HCl$ Calcd. (%): C, 67.67; H, 6.63; N, 9.86 Found (%): C, 67.30; H, 6.58; N, 9.72.

Reference Example 29

2-(4-Hydroxyphenyl)-4-methyl-6-[3-(4-phenylpiperidino) propoxyl]pyrimidine hydrochloride m.p. 229–230.5° C.

Elemental analysis for $C_{25}H_{29}N_3O_2 \cdot HCl$ Calcd. (%): C, 68.25; H, 6.87; N, 9.55 Found (%): C, 67.91; H, 7.01; N, 9.64.

Reference Example 30

4-(4-Hydroxyphenyl)-2-methyl-6-[3-(4-phenylpiperazino) propoxy]pyrimidine maleate m.p. 210° C.

Elemental analysis for $C_{24}H_{28}N_4O_2 \cdot C_4H_4O_4$ Calcd. (%): C, 64.60; H, 6.20; N, 10.76 Found (%): C, 64.20; H, 6.47; N, 10.36.

Reference Example 31

2-(4-Hydroxyphenyl)-4-methyl-6-[3-[4-phenylpiperazino) propoxy]pyrimidine hydrochloride m.p. 253–254° C.

Elemental analysis for $C_{24}H_{28}N_4O_2 \cdot HCl$ Calcd. (%): C, 65.37; H, 6.63; N, 12.71 Found (%): C, 64.98; HI 6.73; N, 12.33.

Reference Example 32

4-(4-Fluorophenyl)-2-methyl-6-[2-[4-(2-methoxyphenyl) piperazino]ethoxy]pyrimidine hydrochloride m.p. 193.0–194.5° C.

Elemental analysis for $C_{24}H_{27}FN_4O_2 \cdot HCl$ Calcd. (%): C, 62.81; H, 6.15; N, 12.21 Found (%): C, 62.68; H, 6.18; N, 12.34.

Reference Example 33

4-(4-Fluorophenyl)-2-methyl-6-[2-(4-phenylpiperazino) ethoxy]pyrimidine hydrochloride m.p. 201–204° C.

Elemental analysis for $C_{23}H_{25}FN_4O \cdot HCl$ Calcd. (%): C, 64.40; H, 6.11; N, 13.06 Found (%): C, 64.21; H, 6.10; N, 13.26.

Formulation Example 1

According to the following recipe, an injection, 1 ml, can be prepared in the routine manner.

| Recipe | |
| --- | --- |
| Compound of the invention (Example 1) | 1 mg |
| Sodium chloride | 9 mg |
| Water for injection | q.s. |

Formulation Example 2

According to the following recipe, an injection, 1 ml, can be prepared in the routine manner.

| Recipe | |
|---|---|
| Compound of the invention (Example 2) | 1 mg |
| Glucose | 48 mg |
| Sodium dihydrogen phosphate | 1.25 mg |
| Sodium monohydrogen phosphate | 0.18 mg |
| Water for injection | q.s. |

Formulation Example 3

According to the following recipe, an injection, 1 ml, can be prepared in the routine manner.

| Recipe | |
|---|---|
| Compound of the invention (Example 4) | 1 mg |
| Sorbitol | 48 mg |
| Benzyl alcohol | 20 mg |
| Sodium dihydrogen phosphate | 2.5 mg |
| Sodium monohydrogen phosphate | 0.36 mg |
| Water for injection | q.s. |

Formulation Example 4

According to the following recipe, a tablet, 120 mg, can be prepared in the routine manner.

| Recipe | |
|---|---|
| Compound of the invention (Example 3) | 3 mg |
| Lactose | 58 mg |
| Corn starch | 30 mg |
| Crystalline cellulose | 20 mg |
| Hydroxypropylcellulose | 7 mg |
| Magnesium stearate | 2 mg |

Test Example 1

Delayed Neuronal Death (DND) Inhibitory Activity in Gerbils

The delayed neuronal death protective effect of the compound of the invention was confirmed by an experiment using gerbils. This test is the most widely used for all relevant in vivo evaluation protocols and it is reported that any drug showing DND inhibitory activity in this test system can be expected to be clinically effective in humans [GENDAI-IRYO, 24, 129–133 (1992), Neurology 1987, 37, 1281–1287].

Experimental

Male gerbils weighing 60–80 g were anesthetized with pentobarbital sodium 35 mg/kg i.p. and placed in supine position. After the skin in the cervical region was incised, the bilateral common carotid arteries were exposed and sutures were placed around each artery. Both ends of each suture was introduced into a polyethylene tube and in suturing the incised wound, the tube was secured to the cervical skin with the suture emerged from the other end of the tube. On the following day, with the animal under no anesthesia, both ends of the suture were gently pulled out and the carotid artery snared by the suture was urged in a bent position into the tube to thereby occlude the carotid artery. After a transient ischemic loading of 5 minutes' duration by occlusion of the bilateral common carotid arteries, the arteries were reperfused. After 7 days, the brain was excised and fixed. A section centered around the hippocampus was prepared and Nissle-stained with 0.05% cresyl violet and the pyramidal cells in the hippocampal CA-1 subfield were microscopically examined for degeneration and death. The degree of neuronal death was scored according to the following criteria.

Criteria for evaluation of neuronal death in the hippocampal CA-1 subfield

| Score | Degeneration and death of pyramidal cells |
|---|---|
| 0 | 0–10% death (nearly normal) |
| 1 | 10–25% death |
| 2 | 25–50% death |
| 3 | 50–75% death |
| 4 | 75–100% death |

The test drug was dissolved in saline and administered intraperitoneally at the same time as reperfusion following the 5-minute ischemic loading. The results are presented in Table 1.

TABLE 1

| Delayed neuronal death protectivre activity in gerbils | |
|---|---|
| | DND inhibition 50 mg/kg i.p. |
| Control | 4.00 (5) |
| Compound of Example 1 | 0.60 (5)** |
| Compound of Example 2 | 0.80 (5)** |
| Compound of Example 3*1 | 0.60 (5)** |
| Compound of Example 4 | 0.60 (5)** |
| Compound of Example 16 | 0.60 (5)** |
| Compound of Example 18 | 0.80 (5)** |
| Compound of Example 21 | 0.60 (5)** |
| Compound of Reference Example 10 | 0.60 (5)** |

**: $p < 0.01$ (Wilcoxon's U test)
*1: 30 mg/kg, i.p.
The figure in parentheses denotes the number of animals.

It will be apparent from the above results that the compound of the invention markedly inhibited neuronal death in the gerbil model of transient ischemia. Moreover, when administered orally, the compound of the invention inhibited delayed neuronal death. Furthermore, even when the compound of Example 1 was administered in a single dose after a lapse of 1–2 hours after ischemia, it exhibited a protection activity against the delayed neuronal death.

These results indicate that the compound of the invention is not only useful for preventing the onset of sequelae of a cerebrovascular disease but also useful as a therapeutic drug for cerebrovascular disease.

Test Example 2

Protection of Cerebral Infarction in Rats With Middle Cerebral Artery Occlusion

The cerebral infarction protective effect of the compound of the invention was confirmed in a rat middle cerebral artery occlusion model. This is an animal model of brain regional ischemia which is similar to human cerebral infarction and it is known that the model is useful as a therapeutic model as well (Cerebral Apoplexy Experiment Handbook, 91–97, 1990, published by ICP). Any drug showing cerebral infarction protective activity in this test system can be expected to be clinically effective in humans.

Experimental

Male SD rats aged 7–8 weeks were anesthetized with ketamin hydrochloride 120–150 mg/kg, i.p. and the head was placed in lateral recumbent position on an operation table. The skin was linearly incised midway between the external auditory foramen and the outer canthus along the anterior margin of the temporal muscle to the zygoma. Using an electric dental drill, a small hole was drilled midway between the oval foramen and the orbital fissure and the dura mater was incised. The middle cerebral arterial trunk traversing the transverse olfactory nerves (olfactory cord) was electrically coagulated and cut within the olfactory cord using a bipolar electrode and the incision wound was sutured. Two days after the operation, the animal was decapitated and the brain was excised. Then, frontal sections of the brain were prepared at 2 mm intervals from the rostal part of the olfactory bulb. Using a saline solution (2%) of 2,3,5-triphenyltetrazolium chloride (TTC), a compound which is colorless by itself but is enzymatically converted to a red dye in living tissues, the sections were stained at 37° C. for 30 minutes. Then, the frontal sections were photographed and using an image processor, the areas of infarction were measured. The percentage of the infarct area in the frontal section 6 mm caudal to frontal rostrum, that is at the striatal level, relative to the total area of the tissue section and the total infarct area of the 5 frontal sections prepared at 2 mm intervals from the frontal rostrum was calculated and the percentage of the total infarct area relative to the total area of all the sections was calculated. As the test drug, the compound of Example 1 was administered intravenously after middle cerebral artery occlusion. As a result, the compound of the invention at the dose of 0.125 mg/kg markedly inhibited neuronal death in the rat model of persistent brain ischemia.

Test Example 3
NMDA-Induced Convulsion Inhibitory Activity

Mice were intraperitoneally dosed with 200 mg/kg of N-methyl-D-aspartate (NMDA) and observed for the consequent convulsion and death over a period of 30 minutes after administration. As test drugs, the compound of Example 1, compound of Example 2, compound of Reference Example 10, and compound of Reference Example 12 were used and each was administered intraperitoneally 30 minutes before administration of NMDA. As a result, the compound of the invention at 20 mg/kg did not inhibit the NMDA-induced convulsion. These results suggest that the compound of the present invention does not act on the NMDA receptor.

Test Example 4
Acute Toxicity Study

Male SD rats (Slc:SD, Japan SLC) were used. The rats were purchased at 7 weeks of age and the animals which went through a week-long quarantine and acclimation were used in groups of 6. The dose volume was 5 ml/kg for intraperitoneal administration and 10 ml/kg for intravenous administration. Based on the result of a preliminary experiment, the dose range was established to include the mortality rats of 0% and 100%. The drug solutions were prepared using physiological saline and filtered through a 0.22 μm bacterial filter. As test drugs, the compounds of Example 1, Example 2, Example 3, Example 4, Example 16, Example 18, Example 21, and Reference Example 10 were respectively administered intraperitoneally and the animals were observed daily for death and general condition for 7 days from the administration day. As a result, no remarkable change was found in the general condition of animals. Incidentally, the intraperitoneal and intravenous $LD_{50}$ values of the compound of Example 1 were 65.8 mg/kg and 22.8 mg/kg, respectively.

INDUSTRIAL APPLICABILITY

As established by the above test results, the compound of the present invention shows an excellent protective activity against neuronal death regardless of whether it is administered simultaneously with the onset of brain ischemia or infarction or administered a few hours following the episode. Moreover, the toxicity of the compound is low. Therefore, the compound of the invention is of great use as a neuronal death inhibitor in the acute phase of a cerebrovascular disease. In addition, the compound is useful as a therapeutic drug for cerebrovascular diseases such as cerebral infarction, cerebral hemorrhage, head trauma and subarachnoid hemorrhage, and further as a medicine which inhibits the onset of sequelae of cerebrovascular diseases (e.g. nervous symptoms such as dyskinesia and convulsion and mental symptoms such as emotional and intellectual disturbances), thus protecting the brain.

We claim:

1. A method of treatment of acute cerebrovascular disorder which comprises the step of administering to a patient in need thereof an effective amount of a compound of the following general formula [I] or a salt thereof, or a solvate thereof, as an active ingredient;

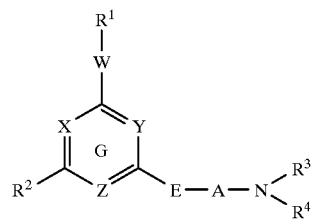

[I]

wherein $R^1$ represents an aryl group that may be substituted; said aryl group may be substituted by 1–3 substitutes, whether the same or different, as selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro;

$R^2$ represents hydrogen, alkyl, alkenyl, cycloalkyl, cycloalkylalkyl, hydroxyalkyl, haloalkyl, alkoxy, alkylthio, amino, monoalkylamino, dialkylamino, or phenyl that may be substituted by 1–3 same or different substitutes selected from the group consisting of halogen, alkyl, and alkoxy;

$R^3$ and $R^4$ taken together with the adjacent N atom represent piperdino, which N, O, or S in addition to said N atom may be substituted by one or more substitutes selected from the group consisting of alkyl, alkoxy, hydroxy, oxo, amino, monoalkylamino, dialkylamino, aryl that may be substituted, and pyridyl that may be substituted;

A represents alkylene of 2–10 carbon atoms, which may be substituted by 1 or 2 same or different substitutes selected from the group consisting of alkoxy, hydroxy, and oxo in optional substitutable positions;

E represents O or S;

W represents a single bond, O, S, or $(CH_2)_n$, where $CH_2$ may be substituted by alkyl; n is an integer of 1 or 2;

two of X, Y, and Z represent N and the other represents CH, CR (where R represents alkyl); thus, ring G represents pyrimidine;

and one of the nitrogens may form an oxide.

2. The method of the treatment of acute cerebrovascular disorder as claimed in claim 1 wherein $R^1$ represents halogen-substituted phenyl; $R^2$ represents alkyl or haloalkyl; —$NR^3R^4$ represents piperidino; A represents alkylene of 3–6 carbon atoms; E represents O or S; W represents a single bond; X and Z respectively represent N with Y representing CH or Z represents CH with X and Y respectively representing N.

3. The method of the treatment of acute cerebrovascular disorder as claimed in claim 1 wherein $NR^3R^4$ represent piperdino; A represents alkylene of 4–6 carbon atoms; E represents O; W represents a single bond; and X and Z respectively represent N with Y representing CH or Z represents CH with X and Y respectively representing N.

4. The method of the treatment of acute cerebrovascular disorder as claimed in claim 1 wherein the active ingredient is a compound selected from the group consisting of 4-(4-fluorophenyl)-2-methyl-6-(4-piperidinobutoxy)pyrimidine, 4-(4-fluorophenyl)-2-methyl-6-(5-piperidinopentyloxy)pyrimidine, 4-(4-fluorophenyl)-2-methyl-6-(6-piperidinohexyloxy)pyrimidine, 4-(4-fluorophenyl)-2-methyl-6-(1-methyl-4-piperidinobutoxy)pyrimidine, and 2-(4-fluorophenyl)-4-methyl-6-(4-piperidinobutoxy) pyrimidine.

5. A method of inhibition of a brain neuronal death comprising administering to a patient in need thereof an effective amount of the compound, salt, or solvate claimed in claim 1 as an active ingredient.

6. A method of prevention of the onset of acute cerebrovascular disorder sequela administering to a patient in need thereof an effective amount of the compound, salt, or solvate claimed in claim 1 as an active ingredient.

7. A compound of formula [I] or a salt thereof, or each solvate thereof:

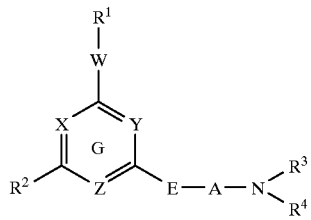

[I]

wherein $R^2$ represents an aryl group that may be substituted; said aryl group may be substituted by 1–3 substitutes, whether the same or different, as selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro;

$R^2$ represents hydrogen, alkyl, alkenyl, cycloalkyl, cycloalkylalkyl, hydroxyalkyl, haloalkyl, alkoxy, alkylthio, amino, monoalkylamino, dialkylamino, or phenyl that may be substituted by 1–3 same or different substitutes selected from the group consisting of halogen, alkyl, and alkoxy;

$R^3$ and $R^4$ taken together with the adjacent N atom represent piperdino, which may be substituted by one or more substitutes selected from the group consisting of alkyl, alkoxy, hydroxy, oxo, amino, monoalkylamino, dialkylamino, aryl that may be substituted, and pyridyl that may be substituted;

A represents alkylene of 4–10 carbon atoms, which may be substituted by 1 or 2 same or different substitutes selected from the group consisting of alkoxy, hydroxy, and oxo in optional substitutable positions;

E represents O or S;

W represents a single bond, O, S, or $(CH_2)_n$, where $CH_2$ may be substituted by alkyl; n is an integer of 1 or 2;

two of X, Y, and Z represent N and the other represents CH, CR (where R represents alkyl); thus, ring G represents pyrimidine;

and one of the nitrogens may form an oxide.

8. The compound claimed in claim 7 wherein, referring to general formula [I], $NR^3R^4$ is piperidino optionally substituted by alkyl, alkoxy, hydroxy, oxo, amino, monoalkylamino, dialkylamino, pyridyl, or aryl; said pyridyl or aryl may be substituted by 1–3 same or different substitutes selected from the group consisting of hydroxy, halogen, alkyl, haloalkyl, hydroxyalkyl, aralkyl, alkenyl, alkoxy, haloalkyloxy, alkylthio cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano and nitro; and A is alkylene of 4–10 carbon atoms.

9. The compound as claimed in claim 7 wherein $R^1$ represents halogen-substituted phenyl; $R^2$ represents alkyl or haloalkyl; —$NR^3R^4$ represents piperdino; A represents alkylene of 4–6 carbon atoms; E represents O or S; W represents a single bond; X and Z respectively represent N with Y representing CH or Z represents CH with X and Y respectively representing N.

10. The compound as claimed in claim 7 wherein $NR^3R^4$ represent piperidino; A represents alkylene of 4–6 carbon atoms; E represents O; W represents a single bond; and X and Z respectively represent N with Y representing CH or Z represents CH with X and Y respectively representing N.

11. The compound as claimed in claim 1 wherein the compound is a compound selected from the group consisting of 4-(4-fluorophenyl)-2-methyl-6-(4-piperidinobutoxy) pyrimidine, 4-(4-fluorophenyl)-2-methyl-6-(5-piperidinopentyloxy)pyrimidine, 4-(4-fluorophenyl)-2-methyl-6-(6-piperidinohexyloxy)pyrimidine, 4-(4-fluorophenyl)-2-methyl-6-(1-methyl-4-piperidinobutoxy) pyrimidine, and 2-(4-fluorophenyl)-4-methyl-6-(4-piperidinobutoxy)pyrimidine, or a salt thereof, or a solvate thereof.

12. A pharmaceutical composition which comprises a compound of formula [I] or a salt thereof, or each solvate thereof, as an active ingredient:

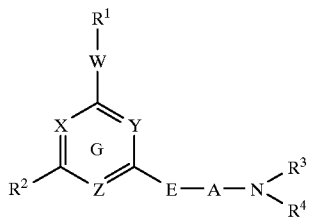 [I]

wherein $R^1$ represents an aryl group that may be substituted;
said aryl group substituted by 1–3 substitutes, whether the same or different, as selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro;

$R^2$ represents hydrogen, alkyl, alkenyl, cycloalkyl, cycloalkylalkyl, hydroxyalkyl, haloalkyl, alkoxy, alkylthio, amino, monoalkylamino, dialkylamino, or phenyl that may be substituted by 1–3 same or different substitutes selected from the group consisting of halogen, alkyl, and alkoxy;

$R^3$ and $R^4$ taken together with the adjacent N atom represent piperidino, which may be substituted by one or more substitutes selected from the group consisting of alkyl, alkoxy, hydroxy, oxo, amino, monoalkylamino, dialkylamino, aryl that may be substituted, and pyridyl that may be substituted;

A represents alkylene of 4–10 carbon atoms, which may be substituted by 1 or 2 same or different substitutes selected from the group consisting of alkoxy, hydroxy, and oxo in optional substitutable positions;

E represents O or S;

W represents a single bond, O, S, or $(CH_2)_n$, where $CH_2$ may be substituted by alkyl; n is an integer of 1 or 2;

two of X, Y, and Z represent N and the other represents CH, CR (where R represents alkyl); thus, ring G represents pyrimidine;

and one of the nitrogens may form an oxide.

13. The pharmaceutical composition as claimed in claim 12, wherein $NR^3R^4$ is piperidino optionally substituted by alkyl, alkoxy, hydroxy, oxo, amino, monoalkylamino, dialkylamino, pyridyl, or aryl; said pyridyl or aryl may be substituted by 1–3 same or different substitutes selected from the group consisting of hydroxy, halogen, alkyl, haloalkyl, hydroxyalkyl, aralkyl, alkenyl, alkoxy, haloalkyloxy, alkylthio, cycloalkyl, cycloalkylalkyl, cycloalkyloxy, alkylsulfonyl, sulfamoyl, alkanoyl, amino, monoalkylamino, dialkylamino, carboxy, alkoxycarbonyl, cyano, and nitro; and A is alkylene of 4–10 carbon atoms.

14. The pharmaceutical composition as claimed in claim 12 wherein $R^1$ represents halogen-substituted phenyl; $R^2$ represents alkyl or haloalkyl; —$NR^3R^4$ represents piperidino; A represents alkylene of 4–6 carbon atoms; E represents O or S; W represents a single bond; X and Z respectively represent N with Y representing CH or Z represents CH with X and Y respectively representing N.

15. The pharmaceutical composition as claimed in claim 12 wherein $NR^3R^4$ represent piperidino; A represents alkylene of 4–6 carbon atoms; E represents O; W represents a single bond; and X and Z respectively represent N with Y representing CH or Z represents CH with X and Y respectively representing N.

16. The pharmaceutical composition as claimed in claim 12 wherein the active ingredient is a compound selected from the group consisting of 4-(4-fluorophenyl)-2-methyl-6-(4-piperidinobutoxy)pyrimidine, 4-(4-fluorophenyl)-2-methyl-6-(5-piperidinopentyloxy)pyrimidine, 4-(4-fluorophenyl)-2-methyl-6-(6-piperidinohexyloxy)pyrimidine, 4-(4-fluorophenyl)-2-methyl-6-(1-methyl-4-piperidinobutoxy)pyrimidine, and 2-(4-fluorophenyl)-4-methyl-6-(4-piperidinobutoxy)pyrimidine, or a salt thereof, or a solvate thereof.

* * * * *

UNITED STATES PATENT AND TRADEMARK OFFICE
CERTIFICATE OF CORRECTION

PATENT NO. : 5,945,426
DATED : August 31, 1999
INVENTOR(S) : Shoichi Chokai; Yojiro Ukai; Tomiyoshi Aoki; Kyoichi Ideguchi It is certified that error appears in the above-identified patent and that said Letters Patent is hereby corrected as shown below:

Column 34, claim 1,
Line 65, delete "piperdino" and after represent insert -- piperidino --;
Lines 65-66, delete "N, O or S in addition to said N atom";
Line 50, delete "substitutes" and insert after 1-3 -- substituents --;
Line 62, delete "substitutes" and insert before selected -- "substituents --;
Line 66, delete "substitutes" and after more insert -- substituents --;

Column 35, claim 1
Line 5, delete "substitutes" and insert after different -- substituents --;

Column 35, claim 3,
Line 27, delete "piperdino" and in its place insert -- piperidino --;

Column 7, claim 7,
Line 65, delete $R^2$ and insert after wherein -- $R^1$ --;
Line 66, delete "substitutes" and insert after 1-3 -- substituents --;

Column 36, claim 7,
Line 11, delete "substitutes" and insert before selected -- substituents --;
Line 14, delete "piperdino" and after represent insert -- piperidino --;
Line 15, delete "substitutes" and insert after more -- substituents --;
Line 19, delete "substitutes" and insert after different -- substituents --;

Column 36, claim 8,
Line 34, delete "substitutes" and insert before selected -- substituents --;

Column 36, claim 9,
Line 43, delete "piperdino" and after $NR^3R^4$ represents insert -- piperidino --;

Column 36, claim 11,
Line 54, delete "1" and insert after claim -- 7 --;

UNITED STATES PATENT AND TRADEMARK OFFICE
CERTIFICATE OF CORRECTION

PATENT NO. : 5,945,426
DATED : August 31, 1999
INVENTOR(S) : Shoichi Chokai, Yojiro Ukai; Tomiyoshi Aoki; Kyoichi Ideguchi It is certified that error appears in the above-identified patent and that said Letters Patent is hereby corrected as shown below:

Column 37, claim 12,
Line 14, delete "substitutes" and insert after 1-3 -- substituents --;
Line 25, delete "substitutes" and insert before selected -- substituents --;
Line 29, delete "substitutes" and insert before selected -- substituents --;
Line 34, delete "subsitutes" and insert after different -- substituents --;

Column 38, claim 13,
Line 7, delete "subsitutes" and insert after different -- substituents --.

Signed and Sealed this

Sixth Day of November, 2001

Attest:

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO.    : 5,945,426
DATED         : August 31, 1999
INVENTOR(S)   : Shoichi Chokai, Yojiro Ukai, Tomiyoshi Aoki and Kyoichi Ideguchi It is certified that error appears in the above-identified patent and that said Letters Patent is hereby corrected as shown below:

Column 34, claim 1,
Line 65, delete "piperdino" and after represent insert -- piperidino --;
Lines 65-66, delete "N, O or S in addition to said N atom";
Line 50, delete "substitutes" and insert after 1-3 -- substituents --;
Line 62, delete "substitutes" and insert before selected -- "substituents --;
Line 66, delete "substitutes" and after more insert -- substituents --;

Column 35, claim 1
Line 5, delete "substitutes" and insert after different -- substituents --;

Column 35, claim 3,
Line 27, delete "piperdino" and in its place insert -- piperidino --;

Column 35, claim 7,
Line 65, delete "$R^2$" and insert after wherein -- $R^1$ --;
Line 66, delete "substitutes" and insert after 1-3 -- substituents --;

Column 36, claim 7,
Line 11, delete "substitutes" and insert before selected -- substituents --;
Line 14, delete "piperdino" and after represent insert -- piperidino --;
Line 15, delete "substitutes" and insert after more -- substituents --;
Line 19, delete "substitutes" and insert after different -- substituents --;

Column 36, claim 8,
Line 34, delete "substitutes" and insert before selected -- substituents --;

Column 36, claim 9,
Line 43, delete "piperdino" and after $NR^3R^4$ represents insert -- piperidino --;

Column 36, claim 11,
Line 54, delete "1" and insert after claim -- 7 --;

UNITED STATES PATENT AND TRADEMARK OFFICE
CERTIFICATE OF CORRECTION

PATENT NO.   : 5,945,426
DATED        : August 31, 1999
INVENTOR(S)  : Shoichi Chokai, Yojiro Ukai, Tomiyoshi Aoki and Kyoichi Ideguchi It is certified that error appears in the above-identified patent and that said Letters Patent is hereby corrected as shown below:

Column 37, claim 12,
Line 14, delete "substitutes" and insert after 1-3 -- substituents --;
Line 25, delete "substitutes" and insert before selected -- substituents --;
Line 29, delete "substitutes" and insert before selected -- substituents --;
Line 34, delete "subsitutes" and insert after different -- substituents --;

Column 38, claim 13,
Line 7, delete "subsitutes" and insert after different -- substituents --.

This certificate supersedes Certificate of Correction issued on November 6, 2001.

Signed and Sealed this

Third Day of September, 2002

*Attest:*

JAMES E. ROGAN
*Director of the United States Patent and Trademark Office*

*Attesting Officer*